United States Patent [19]

Thompson

[11] Patent Number: 5,697,931
[45] Date of Patent: Dec. 16, 1997

[54] APPARATUS AND METHOD FOR LAPAROSCOPIC URETHOPEXY

[75] Inventor: Ronald J. Thompson, Ft. Thomas, Ky.

[73] Assignee: Incont, Inc., Ft. Thomas, Ky.

[21] Appl. No.: 490,281

[22] Filed: Jun. 14, 1995

[51] Int. Cl.$^6$ .................................................. A61B 17/56
[52] U.S. Cl. .......................... 606/72; 606/144; 606/232; 128/DIG. 23; 128/DIG. 25; 128/898
[58] Field of Search ................ 606/72, 75, 113, 606/139, 144, 219, 220, 232; 600/30; 128/898, DIG. 23, DIG. 25

[56] References Cited

U.S. PATENT DOCUMENTS

| | | |
|---|---|---|
| 3,577,991 | 5/1971 | Wilkinson . |
| 3,877,434 | 4/1975 | Ferguson et al. . |
| 4,632,100 | 12/1986 | Somers et al. . |
| 4,669,473 | 6/1987 | Richards et al. . |
| 4,694,826 | 9/1987 | Chester . |
| 4,738,255 | 4/1988 | Goble et al. . |
| 4,827,928 | 5/1989 | Collis, Jr. ............................ 606/79 |
| 4,898,156 | 2/1990 | Gatturna et al. . |
| 4,899,743 | 2/1990 | Nicholson et al. . |
| 4,901,712 | 2/1990 | Voegell et al. ....................... 606/75 |
| 4,938,760 | 7/1990 | Burton et al. . |
| 4,946,468 | 8/1990 | Li . |
| 4,968,315 | 11/1990 | Gatturna . |
| 5,002,550 | 3/1991 | Li . |
| 5,007,894 | 4/1991 | Enhorning . |
| 5,013,292 | 5/1991 | Lemay . |
| 5,013,316 | 5/1991 | Goble et al. . |
| 5,019,032 | 5/1991 | Robertson . |
| 5,037,422 | 8/1991 | Hayhurst et al. . |
| 5,041,129 | 8/1991 | Hayhurst et al. . |
| 5,046,513 | 9/1991 | Gatturna et al. . |
| 5,078,730 | 1/1992 | Li et al. . |
| 5,084,058 | 1/1992 | Li . |
| 5,087,263 | 2/1992 | Li . |
| 5,100,417 | 3/1992 | Cerier et al. . |
| 5,112,344 | 5/1992 | Petros ............................. 128/DIG. 25 |
| 5,133,723 | 7/1992 | Li et al. . |
| 5,135,528 | 8/1992 | Winston ............................ 606/79 |

(List continued on next page.)

FOREIGN PATENT DOCUMENTS 1093329  4/1983  U.S.S.R. .

OTHER PUBLICATIONS

Salerno; Using the Laparoscope for SUI.
Benderev; A Modified Percutaneous Outpatient Bladder Neck Suspension System.
Mitek; Retropubic Bladder Neck Suspension System.
Anchor Fixation and Other Modifications of Endoscopic Bladder Neck Suspension. Theodore V. Benderev, MD, *Urology*, (Nov. 1992) vol. 40, No. 5, pp. 409–418.
Bladder Neck Suspension for Needle Suspension Techniques, Mitek®Surgical Products, Inc. brochure (Aug. 1993).

(List continued on next page.)

*Primary Examiner*—Michael Buiz
*Assistant Examiner*—Mark S. Leonardo
*Attorney, Agent, or Firm*—Dinsmore & Shohl

[57] ABSTRACT

A surgical method for performing laparoscopic urethropexy on a patient is provided. This surgical method comprises the steps of dissecting at least a portion of the space of Retzius in the patient, laparoscopically creating a bore in the pubic bone adjacent the space of Retzius, providing at least one anchor having at least one suture extending therefrom, laparoscopically inserting the anchor in the bore such that the anchor is thereby secured in the bore, and securing the suture to the periurethral tissue adjacent to the urethra to thereby elevate the urethra to the desired angle. The suture is secured to the periurethral tissue by pulling the suture through the periurethral fascia and vaginal mucosa into the vagina, and tying the suture within the vagina. A drill tamper tool for laparoscopically creating the bore in the pubic bone is also provided, along with an anchor-insertion tool, a loaded anchor-insertion tool, and a surgical kit comprising the drill tamper tool and the anchor-insertion tool.

60 Claims, 11 Drawing Sheets

U.S. PATENT DOCUMENTS

| | | |
|---|---|---|
| 5,141,520 | 8/1992 | Goble et al. . |
| 5,147,362 | 9/1992 | Goble . |
| 5,163,946 | 11/1992 | Li . |
| 5,174,087 | 12/1992 | Bruno . |
| 5,176,682 | 1/1993 | Chow . |
| 5,192,303 | 3/1993 | Gatturna et al. . |
| 5,207,679 | 5/1993 | Li . |
| 5,217,486 | 6/1993 | Rice et al. . |
| 5,222,977 | 6/1993 | Esser . |
| 5,224,946 | 7/1993 | Hayhurst et al. . |
| 5,236,445 | 8/1993 | Hayhurst et al. . |
| 5,250,055 | 10/1993 | Moore et al. . |
| 5,258,016 | 11/1993 | DiPoto et al. ............................ 606/75 |
| 5,268,001 | 12/1993 | Nicholson et al. . |
| 5,269,809 | 12/1993 | Hayhurst et al. . |
| 5,281,237 | 1/1994 | Gimpelson . |
| 5,306,290 | 4/1994 | Martins et al. . |
| 5,314,433 | 5/1994 | Li . |
| 5,318,577 | 6/1994 | Li . |
| 5,354,298 | 10/1994 | Lee et al. . |
| 5,356,413 | 10/1994 | Martins et al. . |
| 5,358,511 | 10/1994 | Gatturna et al. . |
| 5,364,410 | 11/1994 | Failla et al. . |
| 5,372,599 | 12/1994 | Martins . |
| 5,376,096 | 12/1994 | Foster . |
| 5,397,325 | 3/1995 | Della Badia . |
| 5,411,506 | 5/1995 | Goble et al. . |
| 5,411,523 | 5/1995 | Goble . |
| 5,417,712 | 5/1995 | Whitaker et al. . |
| 5,423,860 | 6/1995 | Lizardi et al. . |
| 5,437,675 | 8/1995 | Wilson ...................................... 606/80 |
| 5,439,467 | 8/1995 | Benderev et al. . |
| 5,441,502 | 8/1995 | Bartlett . |
| 5,486,197 | 1/1996 | Le et al. . |
| 5,496,345 | 3/1996 | Kieturakis et al. . |
| 5,505,735 | 4/1996 | Li . |
| 5,505,736 | 4/1996 | Reimels et al. . |
| 5,507,796 | 4/1996 | Hasson . |
| 5,520,696 | 5/1996 | Wenstrom, Jr. . |
| 5,520,700 | 5/1996 | Beyar et al. . |
| 5,522,845 | 6/1996 | Wenstrom, Jr. ......................... 606/232 |
| 5,540,711 | 7/1996 | Kieturakis et al. . |
| 5,544,664 | 8/1996 | Benderev et al. . |

OTHER PUBLICATIONS

Extraperititoneal Endoscopic Vesicourethral Suspension (EEVUS), Adley and Peter Albert; Current Surgical Techniques in Urology, Medical Publications, Inc., (1993), vol. 6, Issue 5, pp. 1–8.

Special Report: Laparoscopic Hysterectomy with Bilateral Salpingo–oophorectomy Using a Single Umbilical Puncture, Marco A. Pelosi, MD, et al., New Jersey Medicine, vol. 88, No. 10 (1988) pp. 721–726.

Laparoscopic Retropubic Colposuspension (Burch Procedure), C. Y. Liu, M.D. (Mar. 1993) pp. 1–12.

Laparoscopic Retropubic Cystourethropexy, Ceana H. Nezhat, M.D., et al., The Journal of the American Association of Gynecologic Laparoscopists (Aug. 1994) vol. 1, No. 4, Part 1, pp. 339–349.

The Marshall Marchetti–Krantz Surgical Technique for Urinary Stress Incontinence, Kermit E. Krantz, M.D., Litt. D., Mitek®Surgical Products, Inc. brochure (Aug. 1994).

A Modified Percutaneous Outpatient Bladder Neck Suspension System, Theodore V. Benderev, The Journal of Urology (Dec. 1994) vol. 152, pp. 2316–2320.

New Help for an Old Problem, Sue MacDonald, The Cincinnati Enquirer, Tempo Section E (Wednesday, Mar. 15, 1995) pp. E1 and E3.

Retropubic Bladder Neck Suspension System, Mitek®Surgical Products, Inc., brochure (Nov. 1994) Rev. B.

Spacemaker™ Surgical Balloon Dissector, General Surgical Innovations, Inc. brochure (1994).

Using the laparoscope for SUI, Robert L. Salerno, MD, Ph.D., Contemporary OB/GYN (Dec., 1994) pp. 35–40.

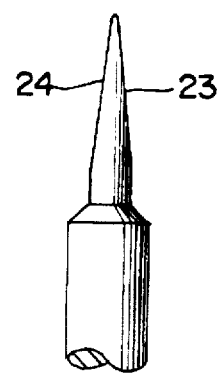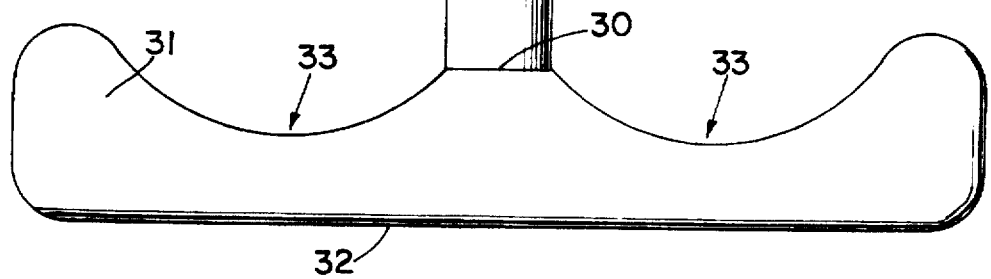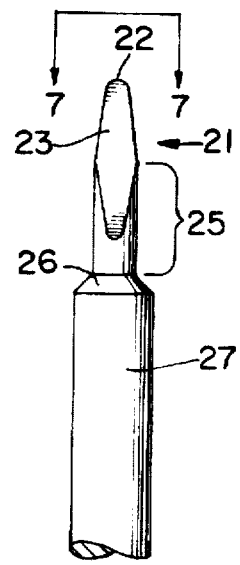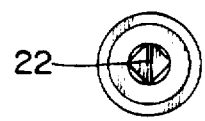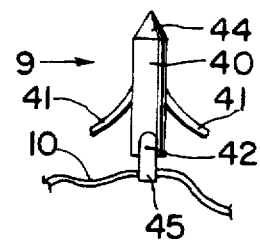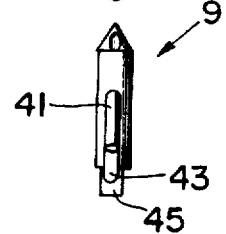

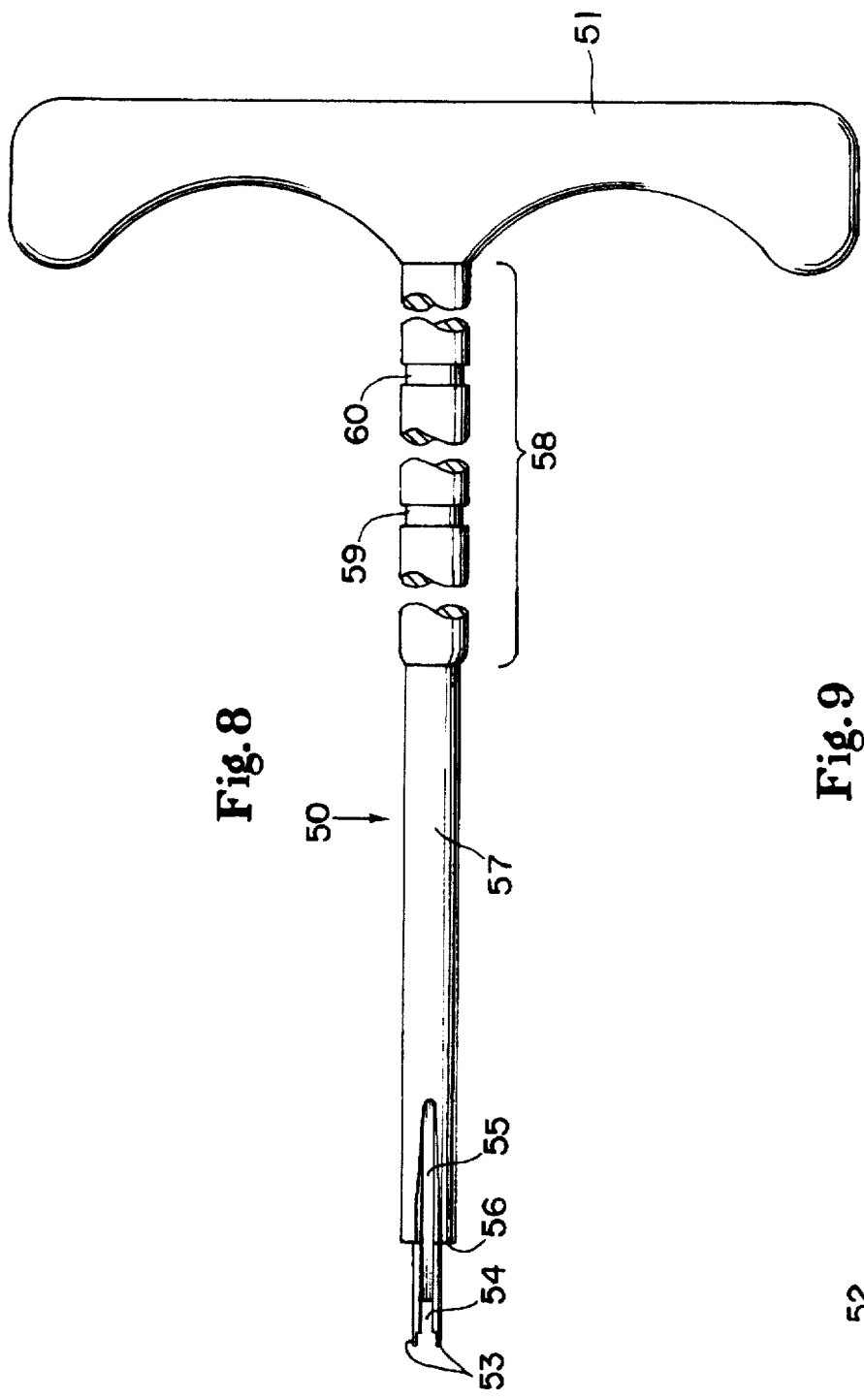
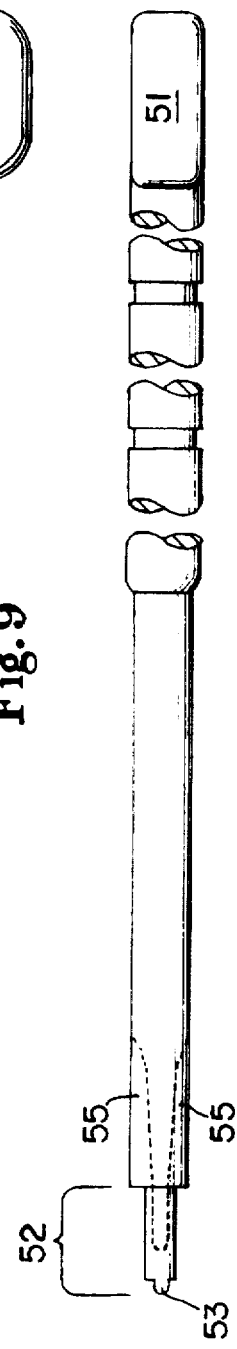
Fig. 8
Fig. 9

APPARATUS AND METHOD FOR LAPAROSCOPIC URETHOPEXY

BACKGROUND OF THE INVENTION

1. Field of the Invention

The present invention is directed towards apparatus and methods for a laparoscopic urethropexy procedure for the correction of female stress urinary incontinence. More particularly, the present invention provides apparatus and methods for performing the urethropexy through laparoscopic techniques, thereby greatly reducing the duration, discomfort, and recovery period of such surgeries.

2. Description of Related Art

Female stress urinary incontinence (SUI), defined as the unintentional loss of urine, can be a socially unacceptable problem for many women. Most often, the incontinence occurs during coughing, sneezing, or physical activity in women afflicted with this problem. While effective surgical treatment for this condition has existed for nearly 50 years, the procedures typically involve major abdominal surgery with accompanying post-operative limitations lasting six to eight weeks. Because of the nature of these surgical procedures, many women simply resort to diaper-like incontinence pads, or simply avoid any activities which result in the unintentional loss of urine.

In the normal resting state, the external pressure exerted on the collapsible urethra by the surrounding musculature is greater than the pressure exerted on the bladder, and therefore continence is maintained. During moments of coughing, sneezing, or physical activities, greater pressure will be exerted on the dome of a filled bladder. In women not afflicted with stress incontinence, a corresponding increase in the external pressure on the urethra acts to prevent the unwanted loss of urine from the bladder. Sufferers of SUI, however, aren't so fortunate.

Stress incontinence is generally caused by two etiologies: a spastic detrusor muscle; or a loss of support of the periurethral tissue at the urethrovesicular junction ("UVJ"— the region where the urethra enters the bladder). When the latter situation occurs, the UVJ will sag into the vagina, thereby reducing the pressure which can be exerted on the urethra during moments of stress. Diagnosis of any sagging of the UVJ can be easily determined by inserting the tip of a cotton swab into the urethra until it reaches the UVJ. The patient is then asked to bear down as if urinating, and loss of the UVJ support is readily identified by the upward movement of the wooden end of the cotton swab. In this test, the external urethral meatus acts as a fulcrum for the tip of the swab, and the elevation of the opposite end indicates the downward descent of the UVJ. U.S. Pat. No. 4,072,144 provides an alternative device which may be utilized to readily measure the angle of the UVJ in a similar manner.

The first urethropexy procedure for eliminating SUI caused by a sagging urethra was developed in 1948 by Drs. Marshall, Marchetti, and Krantz, and generally involves the fixation of the periurethral tissue at the UVJ on either side of the urethra (MMK procedure). Fixation in the MMK procedure, also known as urethropexy or abdominal culposuspension, is accomplished by suturing the periurethral fascia at the UVJ on either side of the urethra to the periosteum of the pubic bone. The procedure essentially alters the angular relationship between the urethra and bladder by elevating the UVJ, and therefore preventing the sagging of the UVJ when downward pressure is applied to the region by various stresses.

The MMK procedure has been perfected over the years, however the essential principles have remained the same. In 1955 Burch developed the technique of affixing the periurethral fascia bilaterally to Cooper's ligament, thereby resulting in a technically easier procedure because of the previous difficulties in passing a needle through the periosteum of the pubic bone. Although the Burch procedure has been performed laparoscopically, the five-year failure rate for the open Burch procedure is approximately 60%. A laparoscopic Burch procedure is even more problematic since it is extremely difficult and time-consuming to tie sutures laparoscopically.

Alternatively, urological procedures such as that of Stamey, Raz and Peyerra have been developed, however these are typically blind procedures which require the passing of long needles through the rectus fascia to the periurethral fascia utilizing a cystoscope. Although these urological procedures avoid the 10-centimeter midline or Pfannenstiel incision and its required three-day or longer hospital stay, the gynecological procedures of MMK, Burch and others have proven to be the most effective. In fact, the scarring of the urethra and interior bladder as well as the scarring of the periurethral tissues, aids in fixation of all of the involved tissues during the MMK and Burch procedures, thereby assisting in the prevention of incontinence.

Recently, a modified version of the MMK procedure has been developed which utilizes bone anchors secured directly to the pubic bone on either side of the symphysis for fixation of the UVJ. The apparatus for performing this modified MMK procedure are sold by Mitek Surgical Products, Inc. of Norwood, Mass., and a number of U.S. patents concern these products (see, e.g., U.S. Pat. Nos. 5,207,679, 5,217, 486 and 4,899,743). In the Mitek-MMK procedure, a Phannenstiel incision must be made in the abdomen in order to provide access to the space of Retzius. The space of Retzius is in actuality a "potential" space in that it contains various connective tissues and fats which must be dissected in order to provide sufficient access to this region. In fact, this connective tissue, particularly the areolar adventitial tissue, generally breaks down after delivery of a child, and this breaking down of the connective tissue often contributes to the onset of SUI in many women.

Once the space of Retzius has been dissected in the Mitek-MMK procedure, small anchors are secured in the pubic bone on either side of the pubic symphysis. Each of the bone anchors has a suture attached thereto, and these sutures are threaded through the periurethral tissue on either side of the urethra. The sutures are then tied off in the abdomen so that the periurethral tissue is pulled upward, which in turn restores the angle of the urethra at the UVJ, thereby restoring the urethra to its proper location. While the Mitek-MMK procedure is highly effective, it is a lengthy and complicated procedure which can generally only be performed by highly-skilled surgeons.

The present invention offers an alternative to the Mitek-MMK procedures which is not only highly effective, but also may be performed laparoscopically.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 3 is a top plan view of a bone anchor used in the method of the present invention;

FIG. 4 is a side plan view of the bone anchor of FIG. 3;

FIG. 5 is a top plan view of a drill tamper tool of the present invention wherein a portion of the tool has been broken-away;

FIG. 6 is a side plan view of the tamper tool of FIG. 5;

FIG. 7 is an end plan view of the tamper tool of FIG. 5, taken along line 7—7 thereof;

FIG. 8 is a top plan view of a bone anchor insertion tool of the present invention, wherein a portion of the tool has been broken-away;

FIG. 9 is a side plan view of the insertion tool of FIG. 8;

SUMMARY OF THE PREFERRED EMBODIMENTS

Figure 1:
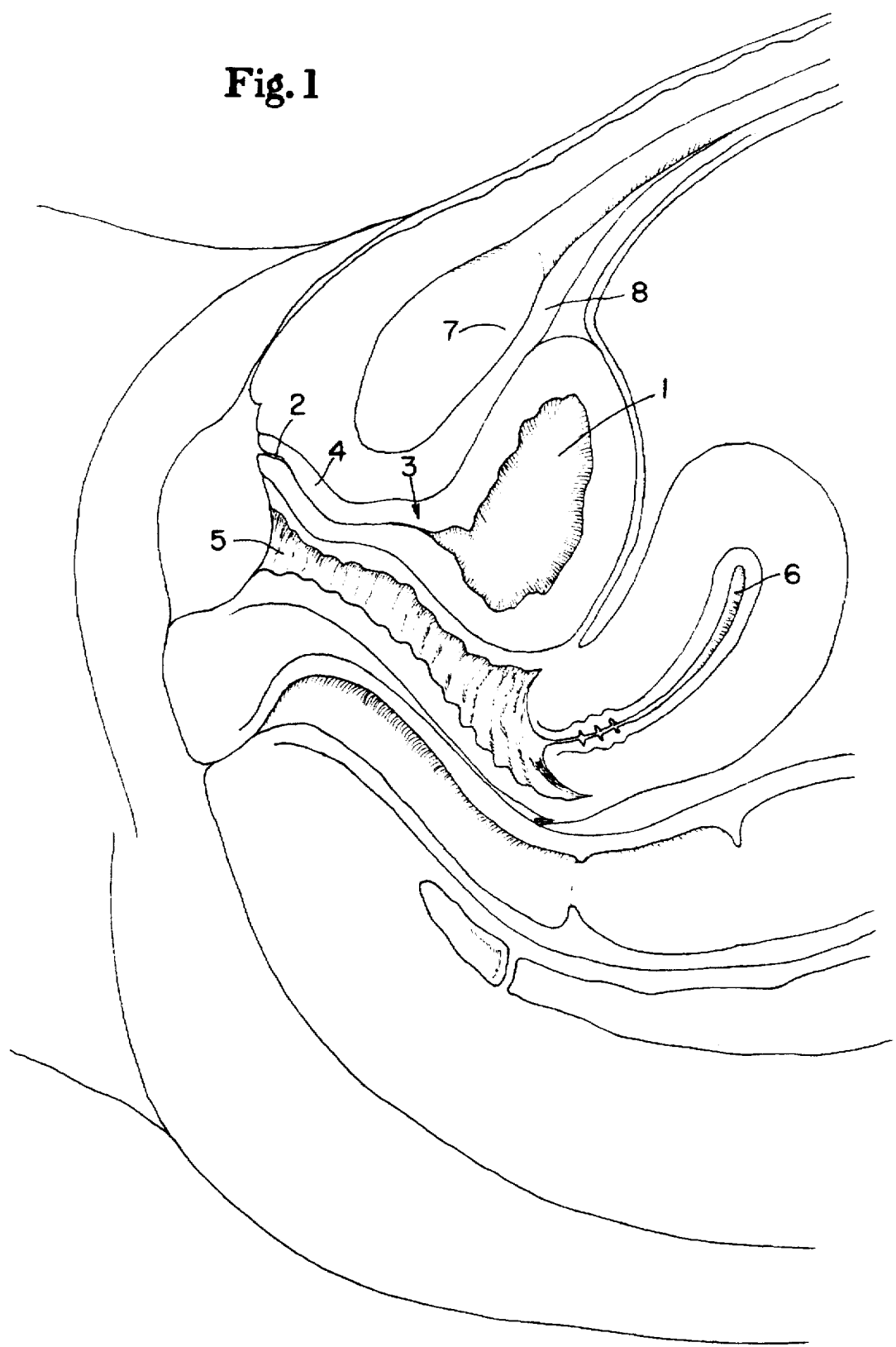
FIG. 1 is a cross-sectional view taken through the midline of a patient who has lost support of the periurethral tissue at the UVJ, and is thereby suffering from stress urinary incontinence.

In accordance with one aspect of the present invention, a surgical method for performing laparoscopic urethropexy on a patient is provided. This surgical method comprises the steps of:

(a) dissecting at least a portion of the space of Retzius in the patient;

(b) laparoscopically creating a bore in the pubic bone adjacent the space of Retzius;

(c) providing at least one anchor, said anchor having at least one suture extending therefrom;

(d) laparoscopically inserting an anchor in said bore such that said anchor is thereby secured in said bore; and (e) securing said suture to the periurethral tissue adjacent to the urethra to thereby elevate the urethra to the desired angle.

The suture is secured to the periurethral tissue by pulling said suture through the periurethral fascia and vaginal mucosa into the vagina, and tying said suture within the vagina. More preferably, a pair of bores are created in the pubic bone, with one of said bores on either side of the pubic symphysis above the periurethral fascia. A pair of anchors are then provided, each of said anchors having a suture extending therefrom, and one of said pair of anchors is inserted into each of said bores (i.e., each bore has an anchor inserted therein). One of said sutures is pulled through the periurethral fascia and vaginal mucosa adjacent either side of the urethra into the vagina, and each of said sutures is then tied within the vagina, such that one of said sutures will provide an upward force on the periurethral tissue positioned on either side of the urethra, thereby elevating the urethra to the desired angle. In other words, the periurethral tissue (preferably both the periurethral fascia and vaginal mucosa) on each side of the urethra will have a suture providing an upward force thereon.

The bore creation step preferably comprises:

(a) inserting a laparoscope into the patient to provide access to and vision of the space of Retzius;

(b) creating a crater in the pubic bone at the desired location for said bore by means of a laser inserted through the laparoscopic channel, said crater being sufficiently deep to provide access to the cancellous bone;

(c) providing a drill tamper tool, said drill tamper tool having a boring tip, said boring tip having a distal end; and (d) inserting said boring tip of said drill tamper tool through the laparoscopic channel;

(e) urging the distal end of said boring tip into said crater to create said bore in the cancellous bone beneath said crater.

The distal end of said boring tip is preferably sufficiently sharp to enable said tip to create said bore in the cancellous bone by means of hand force, while being insufficiently sharp to inadvertently pierce soft tissue or organs during the bore creation step.

The drill tamper tool preferably comprises an elongate rigid member having:

(a) said boring tip, the boring tip being of conical cross section, and having flat sides which taper from said distal end of the boring tip to a cylindrical rear portion of said boring tip, said rear portion having a diameter which corresponds to the diameter of the bore created in the pubic bone;

(b) a collar having a diameter greater than that of the rear portion of said boring tip;

(c) a cylindrical intermediate portion having a diameter greater than that of the rear portion of said boring tip, said intermediate portion attached to said rear portion of said boring tip at said collar;

(d) a cylindrical guide portion having first and second ends, said first end attached to the end of said intermediate portion opposite said collar, said guide portion having a diameter greater than said intermediate portion and slightly less than the operative channel of said laparoscope; and (e) a handle attached to said second end of said guide portion;

wherein said bore is created by inserting said distal end of the boring tip into said crater, and rotatingly urging said boring tip into said crater by means of said handle. The collar acts as a stop during said bore creation step such that the length of said bore is approximately equivalent to the length of said boring tip. While the collar may comprise a conically-shaped portion positioned between the rear portion of the boring tip and the intermediate portion, the collar may also simply comprise the end of said intermediate portion positioned adjacent the cylindrical rear portion of said boring tip.

The dissecting step preferably comprises:

(a) inserting a balloon dissection apparatus infraumbilically into the space of Retzius;

(b) inflating the balloon of said balloon dissection apparatus in order to separate the adventitial tissue in the space of Retzius;

(c) further dissecting the adventitial tissue using a laser, a electrocautery device, or both a laser and a electrocautery device, as needed, wherein the extent of dissection is observed by means of said laparoscope.

The anchor insertion step preferably comprises:

(a) providing an anchor-insertion tool, said anchor-insertion tool comprising a rigid, elongate member having:
an anchor-receiving tip at one end, and
a handle at the opposite end;

(b) loading said anchor on said anchor-receiving tip, with said suture extending along the length of said anchor-insertion tool towards said handle;

(c) inserting said tip of said anchor-insertion tool through the laparoscopic channel;

(d) inserting said anchor into said bore by urging said anchor-receiving tip, with said anchor loaded thereon, toward said bore;

(e) pulling said anchor-insertion tool away from said bore, thereby releasing said anchor from said anchor-receiving tip.

The anchor-insertion tool preferably further comprises an elastic band extending about its circumference. In this fashion, the anchor loading step further comprises positioning said suture between said elastic band and said anchor-insertion tool so that said suture is securely held against said insertion tool by said elastic band. Thus, during said step of pulling said insertion tool away from said bore, said suture is permitted to slide between said elastic band and said insertion tool so that said suture is tensioned between said anchor and said insertion tool to thereby pull outwardly on said anchor in order to seat the anchor within said bore.

The step of pulling said insertion tool away from said bore may also comprise removing said insertion tool at least partially from the laparoscopic channel, so that after said pulling step said suture is tensioned between said anchor and said insertion tool. The suture securing step may then comprise:

(a) providing a suture retriever, said retriever having a pointed tip;

(b) inserting said tip of said suture retriever into the vagina, through the vaginal mucosa and periurethral fascia adjacent the urethra, into the space of Retzius;

(c) snaring said tensioned suture with said suture retriever;

(d) pulling said snared suture into the vagina by means of said suture retriever; and (e) tying said suture within the vagina.

Most preferably the suture has first and second tails, and the tails are pulled into the vagina in this fashion a predetermined distance from each other. The two tails are then tied to each other within the vagina in order to elevate the urethra to the desired angle.

The anchor-insertion tool also preferably further comprises a shouldered depression extending about the circumference of said anchor-insertion tool, wherein said elastic band is positioned within said depression during said anchor loading step. In addition, the insertion tool may comprise a cylindrical intermediate portion having a distal end adjacent said anchor-receiving tip, said intermediate portion having a diameter greater than the diameter of said anchor-receiving tip. The diameter of said anchor-receiving tip is approximately equivalent to the diameter of said anchor; and the combined length of said anchor and said anchor-receiving tip is approximately equivalent to the depth of said bore. In this fashion, during the step of inserting said anchor into said bore, said distal end of said intermediate portion of the anchor-insertion tool acts as a stop, thereby ensuring that the anchor is inserted into said bore to the maximum possible depth.

The present invention also provides a drill tamper tool for laparoscopically creating a bore in the pubic bone of a patient during a urethropexy procedure, said tool comprising an elongate, rigid member having:

(a) a boring tip, said boring tip having a distal end which is sufficiently sharp to enable said tip to create said bore in cancellous bone by means of hand force, while being insufficiently sharp to inadvertently pierce soft tissue or organs during the bore creation step;

(b) a collar having a diameter greater than that of said boring tip;

(c) a cylindrical intermediate portion having a diameter greater than that of said boring tip, said intermediate portion attached to said boring tip at said collar;

(d) a cylindrical guide portion having first and second ends, said first end attached to the end of said intermediate portion opposite said collar, said guide portion having a diameter greater than said intermediate portion, and insertable in the operative channel of a laparoscope; and (e) a handle attached to said second end of said guide portion;

wherein said tool may be employed laparoscopically to create a bore in the pubic bone by inserting said distal end of the boring tip into a crater previously created in said pubic bone, said crater being sufficiently deep to provide access to the cancellous bone, and rotatingly urging said boring tip into said crater by means of said handle in order to create said bore, said bore having a length corresponding to the length of said boring tip.

The boring tip of the drill tamper tool preferably has a conical cross section, and flat sides which taper from said distal end of the boring tip to a cylindrical rear portion of the boring tip, wherein the tool may be employed to create a bore having a diameter which corresponds to the diameter of said rear portion. The total length of said drill tamper tool is such that said tool may be readily employed through a laparoscope in order to create a bore in the pubic bone of a patient during a laparoscopic urethropexy procedure. Preferably, the boring tip has a length of between about 1 and about 3 centimeters, the intermediate portion has a length of between about 2 and about 6 centimeters, and the guide portion has a length of between about 50 and about 55 centimeters.

The present invention also provides an anchor-insertion tool for laparoscopically inserting and securing an anchor within a bore created in the pubic bone of a patient during a urethropexy procedure, said anchor having at least one suture extending therefrom, said anchor-insertion tool comprising an elongate, rigid member having:

(a) an anchor-receiving tip, said tip capable of holding an anchor thereon;

(b) a cylindrical intermediate portion having a distal end adjacent said anchor-receiving tip, said intermediate portion having a diameter greater than the diameter of said anchor-receiving tip;

(c) a cylindrical guide portion having first and second ends, said first end attached to the end of said intermediate portion opposite said distal end, said guide portion having a diameter greater than said intermediate portion, and insertable in the operative channel of a laparoscope; and (e) a handle attached to said second end of said guide portion.

The anchor-insertion tool preferably further comprises at least one shouldered depression extending about the circumference of said tool, said depression sized so as to accommodate an elastic band for holding said suture between said elastic band and said tool. A pair of tapered grooves extending along opposite sides of said tip and at least partially along the length of said intermediate portion are also preferably provided. A second shouldered depression extending about the circumference of said tool may also be provided, said second depression sized so as to accommodate an elastic band for holding said suture between said elastic band and said tool, wherein both of said shouldered depressions extend about said cylindrical guide portion.

The anchor-receiving tip has a pair of guide tabs extending from either side of the end of said tip opposite said intermediate portion, said guide tabs matingly receivable in corresponding grooves on an anchor to thereby hold an anchor on said anchor-receiving tip. The total length of said anchor-insertion tool is such that said tool may be readily employed through a laparoscope in order to insert an anchor in the pubic bone of a patient during a laparoscopic urethropexy procedure. Thus, the intermediate portion may have a length between about 2 and about 6 centimeters, and the guide portion may have a length between about 50 and about 55 centimeters.

The present invention also provides a loaded anchor-insertion tool (i.e., the anchor-insertion tool having an anchor loaded thereon). The anchor may comprise:

a cylindrical body having a conical end;

at least two flexible barbs curving outwardly away from said body;

a cylindrical end portion extending away from said body at an end of said body opposite to said conical end, said end portion having a diameter smaller than said body;

a pair of grooves extending along a portion of the length of said body from said cylindrical end; and an aperture extending through a portion of said cylindrical end and a portion of said body; and The anchor-insertion tool preferably has:

a pair of guide tabs extending from either side of the end of said tip opposite said intermediate portion;

a cylindrical slot extending through a portion of said tip; and a pair of tapered grooves extending along opposite sides of said tip and at least partially along the length of said intermediate portion.

In this fashion, the guide tabs are matingly received in said grooves on said anchor to thereby hold the anchor on said anchor-receiving tip, wherein said suture extends through said aperture on said anchor, and wherein said suture is positioned within said pair of tapered grooves on said anchor-insertion tool.

Finally, a surgical kit for laparoscopically inserting an anchor into the pubic bone of a patient during an urethropexy procedure is provided. This kit preferably comprises the drill tamper tool and the anchor-insertion tool described above.

DETAILED DESCRIPTION OF THE INVENTION

Referring now to the drawings in detail, wherein like numerals indicate identical elements throughout the views, FIG. 1 is a cross-sectional view taken along the midline of a patient suffering from stress urinary incontinence. For reference, FIG. 1 depicts bladder 1, urethra 2, urethrovesicular junction (UVJ) 3, periurethral tissue 4, vagina 5, uterus 6, pubic symphysis 7, and space of Retzius 8. In this patient, urethra 2 and the associated periurethral tissue 4 have sagged into vagina 5. During periods of stress such as coughing or sneezing, pressure will be exerted on bladder 1. Due to the collapse of urethra 2, the surrounding musculature will be unable to provide sufficient counteractive pressure on urethra 2 to prevent loss of urine during these periods of stress. As known from the methods of the prior art, particularly the MMK procedure, fixation of periurethral tissue 4 at UVJ 3 on either side of urethra 2 will act to support the urethra and prevent the sagging of urethra 2 into vagina 5. This in turn will enable the surrounding musculature to provide sufficient pressure on urethra 2 to prevent loss of urine during moments of stress.

Figure 2:
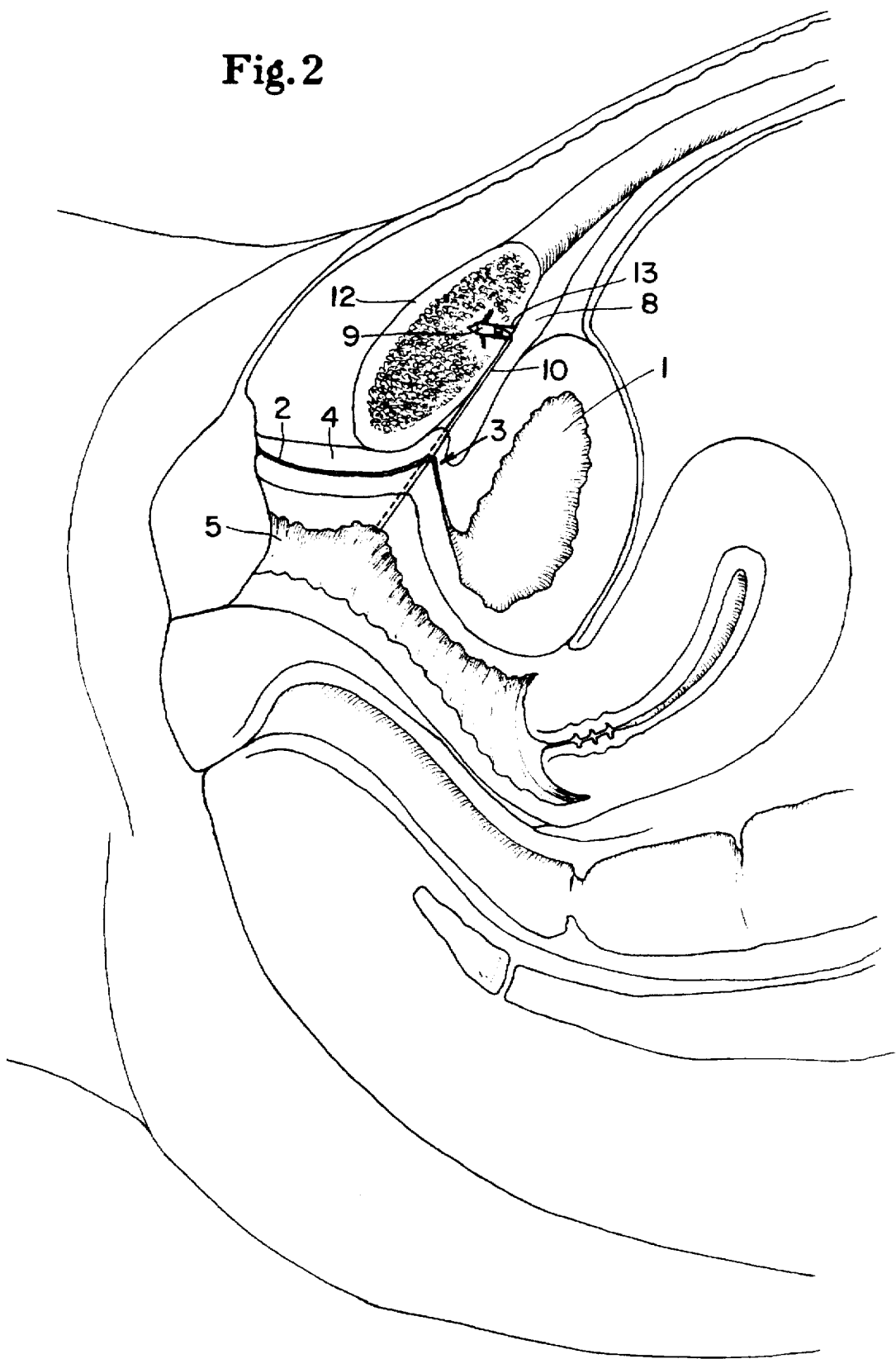
FIG. 2 is the same view as FIG. 1, however the structural defect has been corrected using the method and apparatus of the present invention.

FIG. 2 depicts the resulting support of urethra 2 at UVJ 3 by means of the surgical procedure of the present invention. It should first be noted that pubic bone 12 is shown in FIG. 2, and is that portion of the pubic bone lying immediately to the right of the pubic symphysis. As will be more fully understood later, the anchors of the present invention are secured in the pubic bone on either side of the pubic symphysis. A bore 13 has been produced in pubic bone 12, and anchor 9 has been secured within bore 13. It should be noted that bore 13 and anchor 9 have been enlarged for purposes of clarity. A suture 10 is secured to anchor 9, and the two tails of suture 10 extend downwardly through the space of Retzius 8 into vagina 5. The tails of suture 10 extend into the vagina immediately to the right of urethra 2 through periurethral tissue 4 at UVJ 3. In the vagina, the two tails of suture 10 are tied to one another such that suture 10 provides an upward force on periurethral tissue 4 on the right side of urethra 2 adjacent UVJ 3. An identical anchor and suture combination is secured to the pubic bone on the left side of the pubic symphysis, and the suture enters the vagina in a similar fashion as before in order to provide an upper force on periurethral tissue 4 on the left side of urethra 2. In this fashion, the sutures on either side of the urethra act to restore the angle of the urethra at the UVJ.

As will be described in further detail below, the securing of the anchors to pubic bone 12 can be accomplished laparoscopically. Suture 10 may then be pulled into vagina 5 through periurethral tissue 4 immediately adjacent to urethra 2. The two tails of suture 10 may then be tied to one another within vagina 5 by hand. It has been found that the portion of suture 10 positioned within vagina 5 will be epithelialized within a few days after the procedure. In this fashion, suture 10 will not cause any discomfort or irritation to the patient since suture 10 will quickly be covered by the epithelium of vagina 5.

Surgical Technique

A. Preparatory Procedures

Identification of patients suitable for the techniques of the present invention may be made by any of the known techniques for identifying patients amenable to SUI correction by MMK or similar procedures. For example, as discussed previously a cotton swab may be inserted into the urethra until the end of the swab reaches the UVJ. The patient is then asked to bear down and the movement of the portion of the swab outside of the urethra is monitored. The external urethral meatus will act as a fulcrum for the cotton swab, and a loss of urethral support at the UVJ can be readily identified by the upward movement of the external end of the cotton swab. This indicates a downward descent of the urethra at the UVJ, which in turn provides an indication of the structural cause of the patient's SUI. Other means known in the art, however may be employed to confirm the diagnosis and/or to rule out other possible causes.

The preoperative preparation of the patient follows standard procedures for laparoscopic and gynecological surgeries, however no enema is needed. The patient is placed in the dorsal lithotomy position, and standard parenteral antibiotics are applied. Preferably, the patient is also placed under general anesthesia in order to minimize discomfort.

Figure 17:
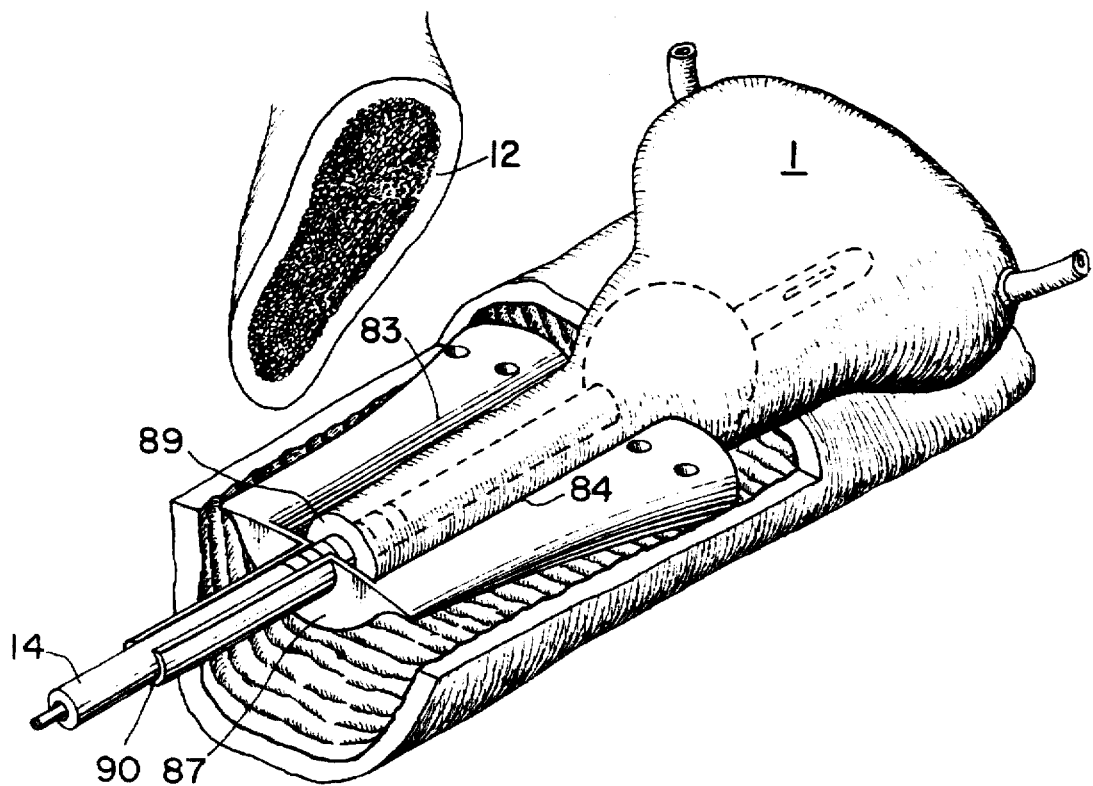
FIG. 17 is a perspective view of the template of FIG. 13 in use during a surgical procedure with portions of the patient's anatomy cut-away for clarity.

A Foley catheter (16 French with 10 cc balloon) is then inserted into the urethra. The balloon of the Foley catheter is inflated, and the catheter is gently pulled outwardly to ensure proper placement of the balloon at the juncture of the bladder and the urethra. Proper placement of Foley catheter 14 is shown in FIG. 17 wherein a portion of vagina 5 has been cut-away for purposes of clarity. Bladder 1 is thereafter drained in the usual fashion using the Foley so that the bladder will become deflated. As will be understood below, maintaining the bladder in a deflated state greatly simplifies the procedure of the present invention. In addition, when the template of the present invention is employed, it is preferable that Foley catheter 14 be positioned in the manner shown in FIG. 17 for reasons which will be described further herein.

It is also desirable to measure the length of the patient's urethra in order to ensure proper placement of the supporting sutures, particularly when the template of the present invention is employed. If the sutures are placed too close to the bladder, there is a considerable risk that the suture retrieving tool will puncture the bladder. Likewise, if the sutures are placed too far from the UVJ, then proper support of the urethra will not be accomplished. The length of urethra 2 may be readily measured by means of any suitable apparatus which may be inserted into the urethra, as long as the surgeon can be certain that one end of the device is positioned at the juncture of the bladder and the urethra (i.e., the UVJ). The simplest means of obtaining this measurement is to provide graduations along at least a portion of the length of Foley catheter 14, as shown in FIG. 17. In this fashion, when the balloon of the Foley is properly inflated within the bladder and the catheter pulled outwardly to ensure proper seating of the balloon at the juncture of the bladder and the urethra, the length of the urethra can be determined using the graduations which will be readily visible immediately adjacent the end of urethra 2. While the average urethra is 3 cm in length, this can often vary between about 2.7 and about 3.3 cm. As will be more fully understood below, the suture template employed in the method of the present invention can thus be manufactured in different sizes to accommodate the differing urethra lengths. A minimum of two sizes for the template may be provided, and more preferably at least three different sizes. Alternatively, the graduations may be employed to facilitate proper placement of a single-sized template.

After the placement of Foley catheter 14 and drainage of bladder 1, an infraumbilical incision is made in the patient in order to provide access to the pre-peritoneal region (the area between the abdominal wall and the peritoneum), and more particularly space of Retzius 8. Surgical dissection of space of Retzius 8 is necessary in order to provide visual access to the pubic bone for placement of the bone anchors. Thus, dissection is performed below the fascia, thereby eliminating the adventitial or supportive connective tissue in space of Retzius 8. Although dissection of the connective tissue in space of Retzius 8 can be accomplished in the typical fashion through a laparoscope, Applicant has found that a balloon dissection procedure is simpler and more effective.

Balloon dissection can be accomplished using the SPACEMAKER surgical balloon dissector manufactured by General Surgical Innovations of Portola Valley, Calif., or an equivalent device. This device has a guide rod to which a small balloon is attached. The guide rod is inserted into the infraumbilical incision until the tip of the rod reaches the pubic symphysis in the space of Retzius (i.e., between the symphysis and the bladder). The balloon is then inflated in space of Retzius 8 by filling the balloon with approximately 300 cc of saline solution or other suitable fluid, thereby further deflating bladder 1 and separating the surrounding connective tissue in order to provide sufficient room in space of Retzius 8 for the fixation procedure of the present invention. The balloon is then aspirated and removed from the pre-peritoneal region.

Although the SPACEMAKER device has an integral trocar which may normally be left in the infraumbilical incision for placement of the laparoscope, the only size currently available is too small for the procedure of the present invention. Obviously a properly sized integral trocar could remain in the patient after removal of the deflated balloon. Alternatively, and as presently preferred, the SPACEMAKER device is removed in its entirety, and a larger 12 mm trocar is inserted into the infraumbilical incision. A 12 mm WOLF operating/laser laparoscope (preferably with a WOLF 50/50 beamsplitter camera) is inserted into the trocar. The pre-peritoneal region is then insufflated, preferably with $CO_2$ at a pressure between about 10 and about 30 mm Hg, thereby further expanding the space of Retzius and providing excellent laparoscopic vision in this region.

Although the balloon dissection procedure is highly effective, further dissection of the space of Retzius is typically necessary in order to provide the necessary access to the pubic bone and the periurethral tissue. Although this may be accomplished by means of a $CO_2$ laser or a electrocautery device through the laparoscope already inserted, it is presently preferred that an additional 5 mm trocar be inserted in the midline suprapubically. A irrigation/suction/bovie device (such as that manufactured by US Surgical) is then inserted into the space of Retzius through the smaller trocar. This device will not only assist in further dissection of the space of Retzius, but will also provide the necessary irrigation and suction while the other instruments necessary for performing the present procedure are employed through the infraumbilical trocar. The result of further dissection is that vision far superior to the standard MMK or Burch procedures employing a full abdominal incision will be provided, since it is difficult in these procedures for the surgeon to see the underside of the pubic bone where the anchors must be placed without the surgeon placing his or her head on the stomach of the patient. In this fashion, unobstructed laparoscopic access to the pubic bone and the periurethral tissue necessary for performing the procedure of the present invention is provided.

B. Creation of Bore in Pubic Bone

It should initially be noted that the procedure of the present invention may be employed with any of a variety of bone anchors, provided that the anchor can be readily secured to the pubic bone and a suture can be attached thereto. It is presently preferred, however, that the MITEK bone anchors known to those skilled in the art be employed for this purpose. As discussed more fully herein, these anchors are secured in place by pressing them into properly-sized bores created in the pubic bone.

Figure 12:
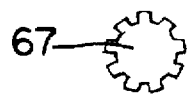
FIG. 12 is an end plan view of the suture retriever of FIG. 11, taken along the line 12—12 thereof.

The MITEK-MMK and related procedures require the use of either a mechanical drill or hand-operated awl in order to provide the bore for insertion of a bone anchor (such as those manufactured by Mitek Surgical Products, Inc.) into the pubic bone. While these devices may be readily employed with large abdominal incisions, they cannot be used through a laparoscope for a number of reasons. Most importantly, these tools must be sufficiently sharp to enable the surgeon to penetrate the hard outer layers of the pubic bone (periosteum and cortical bone). Since the field of vision through a laparoscope may be limited at times, however, it is very risky to employ such sharp implements as there is a tremendous risk of puncturing the bladder or other soft tissue in the operative area. In addition, as best shown in FIG. 12, pubic bone 12 falls away from the laparoscope at an angle of approximately 45°. The angularity of pubic bone 12 therefore provides vision and operative difficulties which are overcome by the apparatus and methods of the present invention. Simply drilling into pubic bone 12 using prior art apparatus through the laparoscope is not advisable because the drill or awl tip will tend to slide downwardly during the drilling operation because of the manner in which pubic bone 12 angles downwardly away from the laparoscope. While the drill tip may eventually penetrate the hard outer periosteum of the bone, the drill may enter at an improper location or angle due to downward slippage of the drill tip. Ideally one would like to produce a bore in pubic bone 12 which is at an angle of approximately 45-degrees to the surface of the bone into which the bore is produced. This angle may, however, be between about 20 and about 60-degrees, to thereby provide sufficient support for the bone anchor to be placed in the bore thus produced.

Applicant has developed a novel method and apparatus for creating the required bores in the pubic bone through a laparoscope. The method and apparatus avoid the use of any sharp tips, while still enabling the surgeon to properly place the bores in the pubic bone without a risk of misalignment during the bore creation process. In order to produce the bore without a need for a sharp instrument, a laser is first employed to produce a cone-shaped crater in the pubic bone at the desired bore location. The crater is produced in the periosteum and cortical bone, thereby providing access to the soft cancellous, or tribecular, bone. In this fashion, a drill tamper tool (to be described further herein) may then be employed to create the properly-sized bore.

Figure 21:
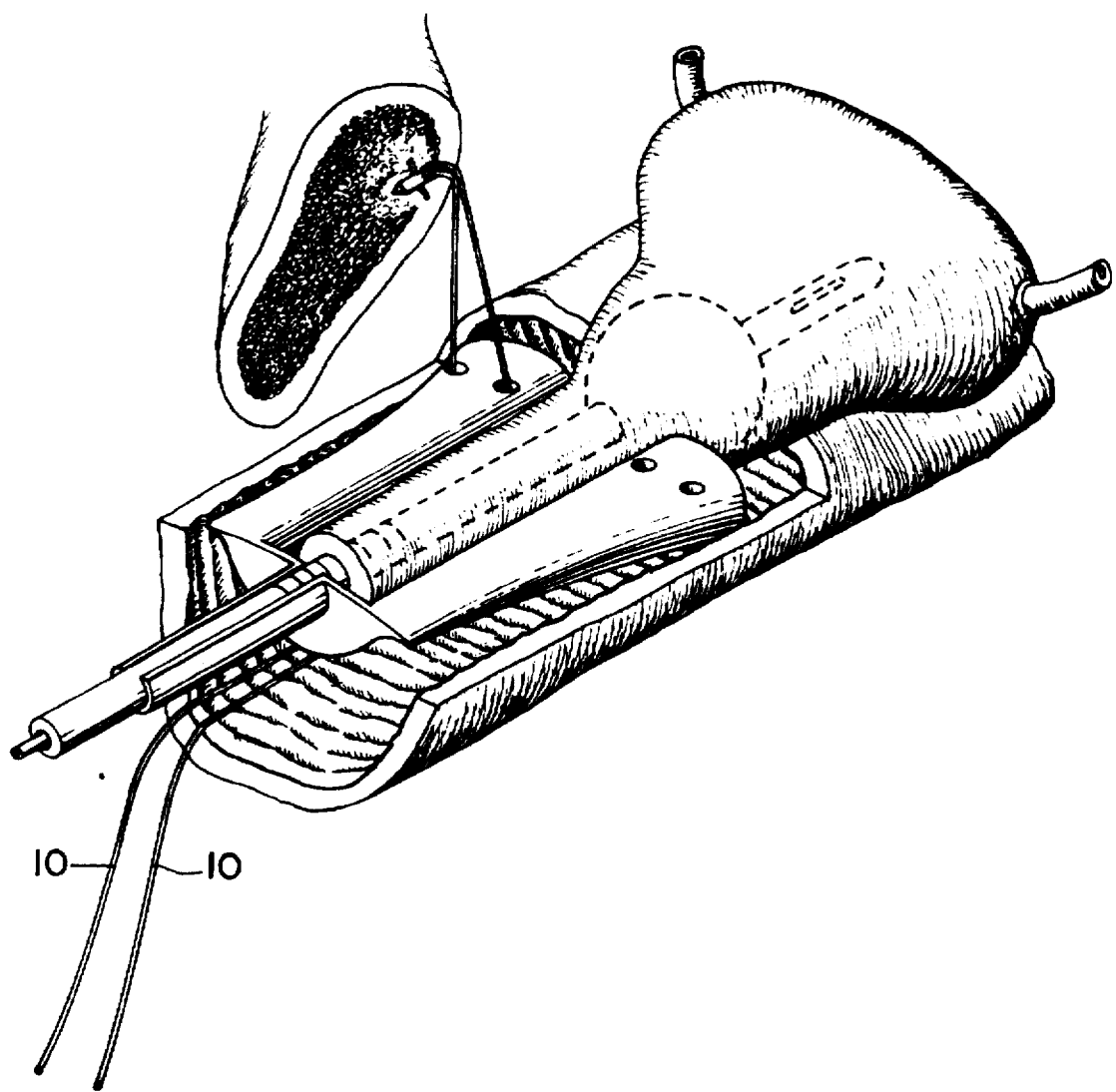
FIG. 21 is a perspective view of the surgical procedure of the present invention wherein portions of the patient's anatomy cut-away for clarity, and wherein the sutures have been retrieved from the pre-peritoneal region for tying.
Figure 22:
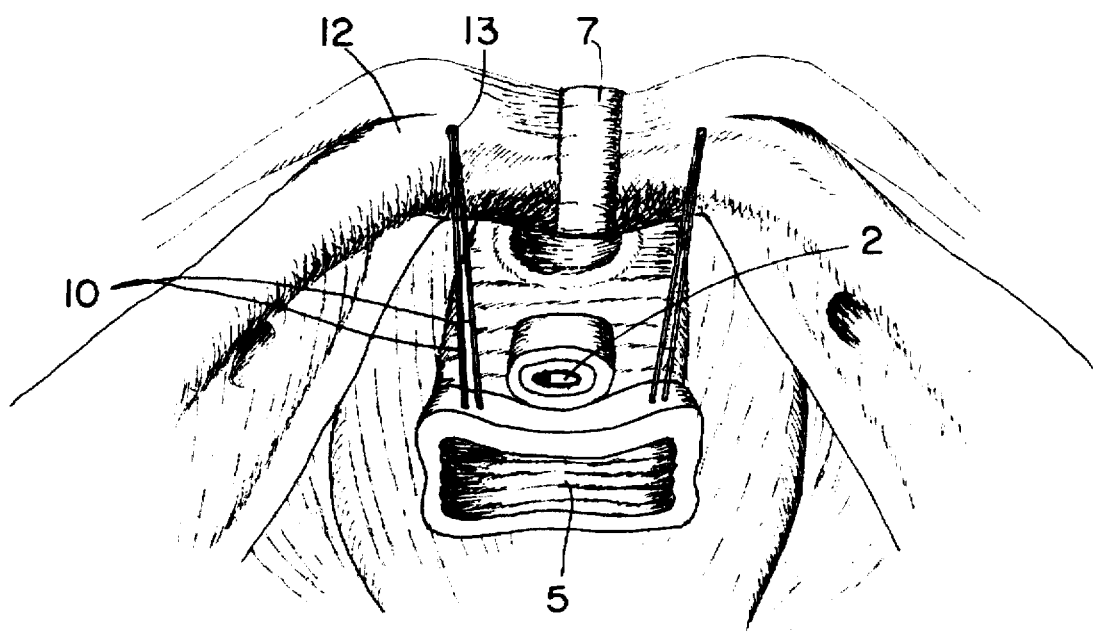
FIG. 22 is a perspective view of the space of Retzius, and illustrates the proper placement of the anchors and sutures employed in the present invention.

In order to create the starter "crater" in the pubic bone, a $CO_2$ laser (such as a SHARPLAN 20 watt) is inserted through the laparoscopic channel, and is employed to create a cone-shaped crater slightly larger than the diameter of the laser beam in the pubic bone on either side of the pubic symphysis. The diameter of the laser beam is preferably about 2 mm, and therefore the cone-shaped crater created in the pubic bone is slightly larger than 2 mm in diameter. The crater should be sufficiently deep to reach the cancellous bone. A crater is established on either side of the pubic symphysis directly above and approximately 1 cm lateral to the periurethral fascia at the UVJ. FIG. 21 depicts the space of Retzius after creation of bores 9 and 17 in pubic bone 12 on either side of pubic symphysis 7. The desired placement location can be readily determined through means of the optics of the laparoscope, as proper dissection of space of Retzius 8 will provide sufficient vision for proper identification of the appropriate structures in the patient. If needed, the surgeon may use one or more fingers to press upwardly on the periurethral tissue on either side of the urethra within the vagina in order to properly position the two starter craters in the pubic bone.

Once access to the cancellous bone has been provided by the cone-shaped craters created on either side of the pubic symphysis using the laser, the bore for insertion of the anchor may be readily created using the drill tamper tool of the present invention. Since the cancellous bone is significantly softer than the periosteum or cortical bone, it is not necessary that a sharp awl or drill bit be used to create the bore. Rather, a bluntly pointed drill tamper tool may be used, wherein the end of the tamper tool is not sufficiently sharp to puncture the bladder or other soft tissue under normal use. This provides a significant advantage in that damage to the bladder or other soft tissue structures and the patient may be readily avoided, and drill guides and the like which must be used with the MITEK Instruments and similar apparatus can be avoided. As will be understood, the MITEK drill guides cannot possibly be employed laparoscopically. The laser employed to create the cone-shaped craters can be readily aligned in the proper location, without risk of slippage or other inadvertent movement during the procedure. The laser-created craters can then be readily employed to insure that the bores for anchor placement are created in the exact, desired location.

The drill tamper tool of the present invention is shown in FIGS. 5–7, and comprises an elongate rigid member 20 having a distal end which comprises a conical boring tip 21. End 22 of conical boring tip 21 preferably has a cross section similar in size and shape to the crater created in the pubic bone by the laser. In this fashion, alignment of conical boring tip 21 within the crater will be relatively easy. It is also preferred that end 22 of conical boring tip 21 be blunt so that it will not penetrate soft tissue such as the bladder during normal use (i.e., not sufficiently sharp to penetrate soft tissue or organs during normal use). Certainly, however, conical boring tip 21 should be sufficiently thin and blade-like to permit boring tip 21 to create the bore in the soft cancellous bone by use of hand force through the laparoscope. In this regard, conical boring tip 21 is preferably shaped similar to a flat bladed screwdriver. Thus, boring tip 21 has tapered side surfaces 23 and 24 which terminate in portion 25 which is of a circular cross-section. The diameter of circular-cross-section portion 25 is identical to the diameter of the bore which will be created in the pubic bone. By rotating the drill tamper tool while simultaneously pressing boring tip 21 into the crater in the pubic bone, the desired bore will be readily created therein. The diameter of portion 25 is also approximately the same as the body of the anchor to be inserted into the bore.

In order to ensure sufficient support for the bone anchors of the present invention, it is also important that the anchor be seated deep within the pubic bone. In order to ensure proper depth of the bore, therefore, collar 26 is provided on the drill tamper tool. Collar 26 is of a larger diameter than conical boring tip 21, and therefore will act as a stop preventing further penetration of the drill tamper tool into the bone. Although collar 26 is shown as tapering in diameter between conical boring tip 21 and intermediate portion 27, it is also possible that collar 26 simply comprise a non-tapered end of intermediate portion 27. Intermediate portion 27 has a diameter significantly greater than that of conical boring tip 21, and is positioned on the opposite end of collar 26. Intermediate portion 27 not only allows the provision of collar 26, but also adds rigidity to the tamper tool. Intermediate portion 27, however, should be significantly smaller in diameter than the operative channel of the laparoscope so that sufficient vision of the operative region is provided. Preferably, the length of conical boring tip 21 is between about 1, and 3 cm, and most preferably about 1.4 cm. Intermediate portion 27 is preferably between about 2, and 6 cm, and most preferably about 5 cm.

In order to provide stability during the boring procedure, cylindrical guide portion 28 is also included on the drill tamper tool. Guide portion 28 has first end 29 and second end 30. First end 29 is attached to intermediate portion 27 at the opposite end of collar 26. Cylindrical guide portion 28 preferably has a diameter slightly less than the operative channel of the laparoscope. In this fashion, guide portion 28 provides the necessary stability within the laparoscope to ensure proper placement of the bores. Second end 30 of guide portion 28 is preferably attached to handle 31. While handle 31 is shown as having a flat end portion 32 and curved hand grip surfaces 33, handle 31 can be of a variety of forms and still be sufficient for purposes of the present invention. Handle 31 facilitates the proper manipulation of conical boring tip 21 through the laparoscope, and provides a sufficiently firm surface 32 upon which force may be applied to complete the boring operation. Guide portion 28 preferably has a length between about 50 and about 55 cm, and most preferably about 52 cm. The overall length of the drill tamper tool of the present invention therefor permits sufficient access to the pubic bone, while also providing an ergonomically-effective boring operation through the laparoscope and ensuring that the tool does not interfere with the anesthesiologist.

C. Insertion of Bone Anchors in Pubic Bone The preferred anchor for use in the present invention is shown in FIGS. 3 and 4, and is identical to that disclosed in U.S. Pat. No. 5,207,679, which is herein incorporated by reference. Anchor 9, which is preferably made of titanium alloy or other suitable material, has a cylindrical body 40 and a conical end 44 attached thereto. At least two flexible barbs 41 curve outwardly away from body 40. A groove 42 is provided on either side of body 40 at the end opposite to conical end 44. In addition, cylindrical end 45 extends away from body 40 adjacent groove 42. The longitudinal axis of cylindrical end 45 is aligned with the longitudinal axis of body 40. The diameter of cylindrical end 45 is preferably equivalent to the diameter of body 40 within grooves 42 positioned on opposite sides of body 40. As will be understood below, this structure facilitates the attachment of anchor 9 to an insertion tool.

As best shown in FIG. 4, body 40 and cylindrical end 45 have an aperture 43 provided therethrough. Aperture 43 is sized so as to accommodate a suture appropriate for the fixation procedure of the present invention. It is preferred that a size 0 GORE-TEX suture be employed, and thus anchor 9 and its accompanying aperture 43 should be sized accordingly. The use of a GORE-TEX suture is preferred for reasons of strength and non-elasticity. Certainly other types of sutures could be employed if necessary. A portion of suture 10 is shown in FIG. 3 having been inserted through aperture 43.

The insertion of anchor 9 is relatively straightforward, and merely requires that the anchor be pressed completely into the bore which has previously been created in the pubic bone. Preferably, anchor 9 is inserted into the bore in the pubic bone until conical end 44 reaches the distal end of the bore. The bore should be at least as long as the length of anchor 9, however, it is preferably considerably longer to ensure sufficient support for the anchor. As anchor 9 is pressed into the bore, flexible barbs 41 will be compressed against body 40 as they are inserted past the hard periosteum and cortical bone surrounding the bore. Once within the bore, however, flexible barbs 41 will tend to spring back into the soft cancellous bone, thereby securing the anchor in place. A slight tug on the tails of the suture 10 will also cause barbs 41 to further deploy.

Figure 10:
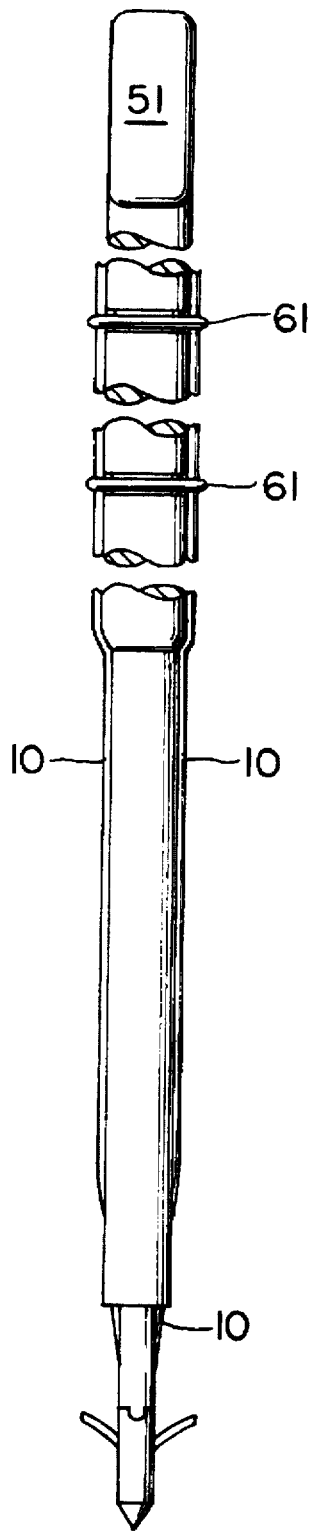
FIG. 10 is a side plan view of the insertion tool of FIG. 8 with the bone anchor of FIG. 3 loaded thereon.

In order to insert anchor 9 into the bore previously created in the pubic bone, the anchor insertion tool shown in FIGS. 8–10 may be employed. Thus, after the drill tamper tool has been employed to create the necessary bores, the anchor insertion tool of the present invention having an anchor and threaded suture loaded thereupon, is inserted into the laparoscope for proper seating of anchor 9.

The anchor insertion tool of the present invention comprises a rigid elongate member 50 having a handle 51 at one end, and an anchor-receiving tip 52 at the opposite end of elongate member 50. As was the case with the drill tamper tool, handle 51 can be of any variety, and that shown is only the presently-preferred embodiment of this handle. Anchor-receiving tip 52 is similar in construction to that shown in FIGS. 4–6 of U.S. Pat. No. 5,207,679. Anchor-receiving tip 52 is constructed so as to matingly receive anchor 9 in order to facilitate insertion of anchor 9 into the bore. As will be apparent, the longitudinal axis of anchor-receiving tip 52 should be aligned with the longitudinal axis of elongate member 50. Anchor-receiving tip 52 is cylindrical in nature, having a diameter approximately equivalent to body 40 of anchor 9. In this manner, at least a portion of anchor-receiving tip 52 may pass through the bore in the pubic bone during the anchor insertion process to properly seat the anchor completely within the bore.

Anchor-receiving tip 52 has a pair of guide tabs 53 extending from the end of anchor-receiving tip 52 on either side thereof. Guide tabs 53 are sized and shaped so as to be matingly received within grooves 42 positioned on either side of anchor 9. Anchor-receiving tip 52 also has a cylindrical slot 54 aligned with the longitudinal axis of tip 52. Cylindrical slot 54 should correspond in size and shape to cylindrical end 45 of anchor 9 in order to matingly receive the same. It is also preferable that the distance between guide tabs 53 be slightly smaller than the distance between the corresponding grooves 42 on anchor 9. In this fashion, guide tabs 53 as well as cylindrical slot 54 will apply compressive force against anchor 9 thereby more securely holding anchor 9 in place when loaded within anchor-receiving tip 52.

Since suture 10 will extend outwardly on either side of anchor 9, it is preferable to provide a means for ensuring that suture 10 is not abraded by the bone surrounding the bore during the insertion process. Thus, a pair of tapered grooves 55 are provided on either side of the anchor insertion tool, and extend from the end of anchor-receiving tip 52 along at least a portion of the length of elongate member 50. As best shown in FIG. 10 wherein anchor 9 has been loaded upon the insertion tool, grooves 55 ensure that the sutures will be protected by anchor-receiving tip 52 and a portion of elongate member 50 during the insertion process. Since any nicks in the suture may compromise the strength and permanency of the fixation, it is important to ensure that the suture is not damaged in any fashion.

Anchor-receiving tip 52 should also be of the proper length to ensure deep placement of anchor 9 completely within the bore. Thus, the length of the combination of anchor-receiving tip 52 and bone anchor 9 when loaded in the manner shown in FIG. 10 should be equivalent to the size of the bore created in the pubic bone. Since the diameter of elongate member 50 is significantly greater than that of anchor-receiving tip 52, distal end 56 of elongate member 50 will firmly abut the pubic bone once the anchor has been completely inserted into the bore. In this manner, the surgeon can be certain that the anchor has been seated to its complete and proper depth.

As was the case with the drill tamper tool of the present invention, elongate member 50 further comprises an intermediate section 57 and a guide portion 58. Intermediate portion 57 should have a diameter sufficiently less than that of the laparoscope in order to provide adequate vision for the surgeon, and intermediate portion 57 also has distal end 56 described above. Preferably, intermediate portion 57 has a length between about 2 and about 6 cm, most preferably about 5 cm. It should be kept in mind that, as shown in FIG. 10, suture 10 will extend along the length of intermediate portion 57 on either side thereof. This consideration must be kept in mind when sizing the diameter of intermediate portion 57 to ensure not only that it can be easily inserted through the laparoscope, but also to ensure adequate vision.

Guide portion 58 will necessarily be slightly smaller than the diameter of the guide portion for the drill tamper tool previously described, since, as shown in FIG. 10, suture 10 will extend along either side of guide portion 58. With this in mind, the total of the diameter of guide portion 58 and twice the diameter of suture 10 should be only slightly less than the inside diameter of the operative channel of the laparoscope. In this fashion, guide portion 28 provides a rigid support for the surgeon during the anchor insertion process. Preferably, guide portion 58 has a length between about 50 and 55 cm., most preferably about 52 cm. This provides an overall inserter length comparable to that of the drill tamper tool, thereby providing the same advantages with regard to the tamper tool length.

In order to effectively employ the procedure of the present invention laparoscopically, it is necessary that the two tails of suture 10 be controlled as much as possible. If the sutures are permitted to hang away from anchor 9 or the anchor insertion tool, the tails will generally become balled within the space of retzius, thereby making the suture tying procedure difficult, if not impossible. Although the sutures may be held against the anchor insertion tool by hand, Applicant has developed a more effective manner of accomplishing this. Thus, first and second shouldered depressions 59 and 60 are preferably provided about the circumference of guide portion 58. A small rubber band 61 (as shown in FIG. 10), or other suitable elastic band, may be held within each of the two shouldered depressions, with the two tails of suture 10 held beneath rubber band 61 on either side of guide portion 58 as shown. First shouldered depression 59 is preferably positioned approximately 10 cm from the ends of guide tabs 53. Second shouldered depression 60 is preferably positioned about 40 cm from guide tabs 53. Both shouldered depressions act, in conjunction with an elastic band contained therein, to hold suture 10 in place on the sides of the anchor insertion tool.

Figure 20:
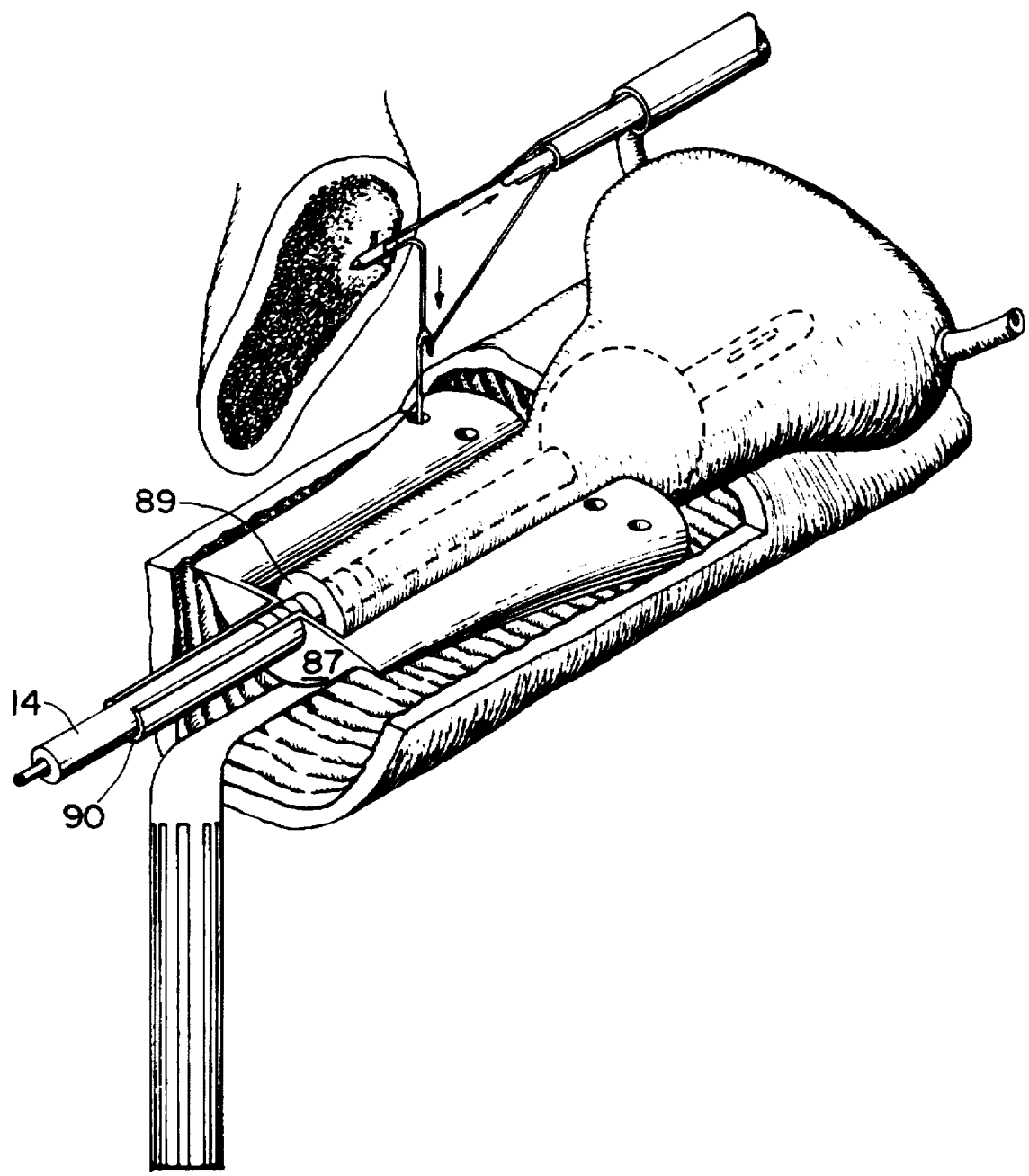
FIG. 20 is a perspective view of the surgical procedure of the present invention wherein portions of the patient's anatomy cut-away for clarity, and wherein the suture retriever of FIG. 11 is being employed.

In addition to holding the suture in place on the anchor insertion tool, the shouldered depression/elastic band combination further improves the laparoscopic procedure of the invention by not only assisting in seating the anchor, but also in the suture retrieval process. As shown in FIG. 20, the anchor insertion tool of the present invention, with a preloaded anchor and suture assembly attached thereto, is inserted through the laparoscope for placement of the anchor as previously described. Once the anchor has been seated within the bore, the anchor insertion tool is then pulled outwardly utilizing handle 51 contained thereon. The combination of shouldered depressions 59 and 60 and rubberband 61 act to provide tension in suture 10 which in turn pulls outwardly on anchor 9 which is now contained in the bore. This outward force on anchor 9 will cause flexible barbs 41 to extend outwardly into the cancellous bone surrounding the bore, thereby further securing anchor 9 in position. In other words, this outward force on suture 10 by the drag created by the shoulder depression/elastic band combination will act to deploy the previously compressed barbs 41 on anchor 9, thereby rigidly securing anchor 9 within the bore.

In order to facilitate the surgical procedure of the present invention, the drill tamper tool and the anchor-insertion tool described above may be provided in the form of a reusable surgical kit.

D. Fixation of Periurethral Tissue at the UVJ Via Suturing

Once the anchor and suture assembly have been secured within the bore created in the pubic bone, it is next necessary to utilize the two tails of the suture to elevate the periurethral tissue on the corresponding side of the urethra at the UVJ. Applicant has found that the most effective means for accomplishing this is to pull each tail of the suture through the periurethral tissue into the vagina. In this fashion, the two tails may then be easily tied to one another within the vagina to provide the necessary support, and eliminating any need for laparoscopic suture tying. Obviously, however, a means for retrieving the suture tails must be provided.

The method of suture retrieval doing is best shown in FIG. 20, which is a perspective view of the procedure with portions of the patient's anatomy cut-away for purposes of clarity. As shown in FIG. 20, as the anchor insertion tool of the present invention is partially withdrawn from the patient through the laparoscope, first shouldered depression 59 in combination with rubberband 61 will cause both suture tails to be tensioned between the anchor and the anchor insertion tool as shown. Were this not the case, the suture tails would merely fall into the space of Retzius similar to a ball of yarn, and thereby be difficult (if not impossible) to retrieve. While the suture tails could be tensioned between the anchor and the anchor insertion tool by pulling outwardly on the sutures, this would unnecessarily require an additional pair of hands. Thus, the shouldered depression/rubber band combination is also effective in this regard.

Once the anchor insertion tool has been partially removed in order to tension the suture tails in the manner shown in FIG. 20, a suture retrieving tool may be inserted into the vagina and then pressed upwardly on one side of the urethra into the space of Retzius in order to retrieve one of the suture tails in the manner shown. Thus, the suture retrieving tool must have a sharp point capable of passing completely through the full thickness of the periurethral fascia and vaginal mucosa adjacent the urethra. The suture retrieval tool must also have a means for grasping the suture tail and pulling the tail back through the full thickness of the periurethral and vaginal mucosa by means of the same entry hole created by the sharp point. Each tail is pulled into the vagina in this fashion at the proper location. Preferably, one tail is pulled into the vagina approximately 1 cm from the urethra at the UVJ, and the other tail is pulled into the vagina approximately 2 cm lateral from the urethra. In other words, each tail penetrates the periurethral tissue along an imaginary line extending substantially perpendicularly away from the urethra. Each tail may then be pulled out of the vagina for purposes of tying.

The suture tails are tied to one another using a series of standard surgeon's knots, and each knot is slid by hand to the point in the vagina at which the suture tails were previously retrieved. The tails are tied to one another in a sufficiently tight fashion so that suture 10 creates an upward force on the periurethral tissue adjacent the urethra in order to elevate the urethra at the UVJ and restore the urethra to its proper angle. The position of the urethra can be readily observed by the surgeon as this procedure is performed, thereby ensuring that the urethra is restored to the desired angle. The entire procedure (anchor insertion, suture retrieval, etc.) is then repeated for the anchor placed on the opposite side of the pubic symphysis, and the suture tails of that anchor are pulled into the vagina through the periurethral tissue on the opposite side of the urethra as the first suture tails. Tying is then performed in the same fashion, thereby elevating the other side of the urethra to thereby completely restore the urethral angle at the UVJ.

The result of this process is best shown in FIG. 2, wherein it is shown that suture 10, and the corresponding suture on the opposite side of the urethra have restored the urethra to its proper angle. It should be noted that at no time do the sutures pull upward directly beneath the urethra, since doing so would create the risk that the suture would cause urethral blockage. After tying, the remaining tails of suture 10 are cut at the knot. The portion of suture 10 remaining in the vagina will epithelize within three to four days, and the patient will no longer sense that the sutures are in place. The result is a permanent fixation of the periurethral tissue on both sides of the urethra, thereby restoring the urethra to its correct angle and eliminating the SUI. After completion of the tying process, the surgical area within the patient is flushed with a dilute lidocaine solution, the laparoscope and trocars removed, a stronger lidocaine solution is applied to the incision sites, and the incisions are closed in the usual fashion. The Foley catheter may then be removed, and the patient permitted to recover in the usual fashion. Normal everyday activities may be resumed within 2-3 days.

E. Suture Retriever

In order to pull the tails of suture 10 through the entire thickness of the periurethral fascia and vagina mucosa, various tools can be employed. For example, a U.S. Surgical Auto-Stitch tool may be effectively employed for this purpose. It is critical, however, that the tool employed being capable of readily be inserted through the periurethral tissue from the vagina into the space of Retzius, while also being capable of grasping the suture tails. It is also critical that the surfaces contacting suture 10 be perfectly smooth in order to eliminate the risk of nicks or cuts in suture 10 which would obviously compromise the effectiveness of the procedure. Applicant has developed a novel suture retriever for accomplishing this purpose which provides a convenient and simple means of retrieving the suture tails.

Figure 11:
FIG. 11 is a side plan view of a suture retriever of the present invention.

The suture retrieval tool of the present invention is depicted in FIG. 11, and comprises metal retrieving end 65, midshaft 66, and handle 67. Midshaft 66 and handle 67 may be singularly molded from polycarbonate or a similar FDA-approved material in the typical fashion. As shown in FIG. 12, handle 67 is also preferably knurled in order to facilitate grasping and manipulation of the retriever. Metal retrieving end 65 is preferably made of stainless steel and can be securely molded into distal end 68 of midshaft 66.

Metal retrieving end 65 comprises a rigid, rod-like shaft 69, and a sharp tip 70 capable of penetrating the periurethral tissue. The diameter of distal end 68 is preferably significantly greater than that of shaft 69, and will act as a stop in order to limit the penetration of the suture retrieval tool into the space of Retzius. Thus, the length of shaft 69 and tip 70 may be selected so as to ensure that when the suture retrieval tool is inserted into the space of Retzius through the vagina that sharp tip 70 will generally be incapable of striking any surrounding soft tissue.

Retrieving end 65 further comprises a return leg 71 which extends away from sharp tip 70 in the same direction of shaft 69. Shaft 69, return leg 71 and the underside of sharp tip 70 thus create an inverted U-shaped region capable of ensnaring suture 10 for retrieval purposes. The distance between return leg 71 and shaft 69 in the region of the inverted U-shape is preferably approximately the same diameter as suture 10. In this fashion, and as shown in FIG. 20, after sharp tip 70 has penetrated the periurethral tissue adjacent the vagina in order to enter the space of Retzius, the inverted U-shape may be pulled downwardly over a suture tail, thereby snaring the suture. Metal retrieving end 65 may then be pulled back through the periurethral tissue, and the tail of suture 10 will remain snared between return leg 71 and shaft 69 directly beneath sharp tip 70. Although the suture tail will slide within the U-shaped region, it will nevertheless be pulled into the vagina.

One critical feature of the suture retriever of FIG. 12 is that the inner surfaces of metal retrieving end 65 which contact suture 10 must be rounded and smooth in order to permit suture 10 to freely slide within the inverted U-shaped portion as the retriever is withdrawn. This prevents nicking or fraying of the suture while still permitting the suture tail to be withdrawn. Thus, the only sharp portion of metal retrieving end 65 is sharp tip 70.

While it is possible that handle 67, midshaft 66, and metal retrieving end 65 may all be positioned along the same longitudinal axis thereby forming a rigid, elongate structure, Applicant has found that the process of the present invention can be simplified if the elements of the retriever have the angular relationship indicated in FIG. 11. This is particularly true when the template of the present invention (to be described further herein) is employed. Thus, metal retrieving end 65 preferably is positioned at an angle of between about 50 degrees and about 80 degrees, most preferably about 60 degrees, to midshaft 66 (this angle is indicated as A in FIG. 11). Likewise, handle 67 is preferably positioned at an angle of between about 50 degrees and about 80 degrees, most preferably about 60 degrees, to handle 67 (this angle is indicated as B in FIG. 11). Thus, the longitudinal axis of shaft 69 of metal retrieving end 65 will be parallel to the longitudinal axis of handle 67. In this fashion, when the retriever of the present invention is employed midshaft 66 will generally be positioned parallel to the longitudinal axis of the vagina. Metal retrieving end 65 will then extend upwardly through the periurethral tissue into the space of Retzius as desired. As best shown in FIG. 20, handle 67 will thereby extend downwardly outside of the vagina, and thus sharp tip 70 may be readily forced through the periurethral tissue as desired merely by pushing upwardly on handle 67.

As shown in FIG. 11, the transitions between handle 67 and midshaft 66 as well as between midshaft 66, and retrieving end 65 should be gently curved in order to ease placement. It should be noted that angles A and B can vary significantly, however it is preferred that they be as close to one another as possible so that the parallel relationship of handle 67 and retrieving end 65 is maintained. In addition, the present configuration ensures that the retrieving end 65 will enter the space of Retzius at an angle of approximately 90 degrees to the tensioned suture tails (i.e., the suture tails tensioned between the anchor and the anchor insertion tool). This perpendicular relationship allows for effective snaring of the suture, as well as improved vision of the retrieval through the laparoscope.

Preferably, midshaft 66 is between about 2 and about 6 cm. in length, most preferably about 4 cm. The cross-sectional area of midshaft 66 should merely be a size chosen to provide the necessary rigidity while also not blocking vision within the vagina during the procedure. Likewise, handle 67 is preferably about 4 cm long, however the length is not as critical since handle 67 remains completely outside of the body. The diameter of handle 67 should be chosen so as to provide a comfortable and secure means of grasping the suture retrieval tool. Preferably, handle 67 is about 3 cm in diameter.

F. Surgical Template

While the placement of the sutures at the UVJ may be accomplished by merely feeling for the correct location within the vagina by hand, particularly in relation to the ball of the Foley catheter, Applicant has developed a novel template which greatly simplifies proper placement of the sutures. This device not only prevents bladder injury, urethral injury, or vascular accidents, the template also ensures a proper distance between the two suture tails to ensure that there is adequate periurethral tissue between the tails to provide the necessary support. Obviously if the suture tails are placed too close to one another, there is a risk that the suture will tear through the periurethral tissue and eliminate the fixation. Thus, a template is provided wherein the template has at least two apertures which may be properly positioned on either side of the urethra. The suture retriever may then be inserted through these apertures and thereafter through the periurethral tissue in order to snare the suture tails in the manner described previously.

The presently preferred template is depicted in FIGS. 13–17. The template comprises a trough 80 of arcuate cross-section, wherein trough 80 is sized so as to cradle the patient's urethra when properly positioned. First and second wing members 81 and 82 extend away from opposite sides of trough 80, preferably perpendicularly to the longitudinally axis of trough 80 in the manner shown. Most preferably wing members 81 and 82 extend perpendicularly away from opposite sides of trough 80 at the upper most edges 83 and 84 of trough 80. First and second suture guide apertures 85 and 86 are positioned in each of the wing members 81 and 82 as shown. The guide apertures are positioned so that when the urethra of the patient is properly positioned within trough 80, guide apertures 85 and 86 on each wing will indicate the proper location for the sutures. First suture guide aperture 85 is positioned so that the first tail of suture 10 will penetrate the periurethral tissue approximately 1 cm from the urethra adjacent the UVJ. Second guide aperture 86 is preferably positioned about 1 cm further away from the urethra along a line perpendicular to the longitudinal axis of trough 80. In other words, the distance between first suture guide aperture 85 and second suture guide aperture 86 is preferably about 1 cm. In this manner, the surgeon can be confident that sufficient periurethral tissue will be present between the two suture tails.

Figure 13:
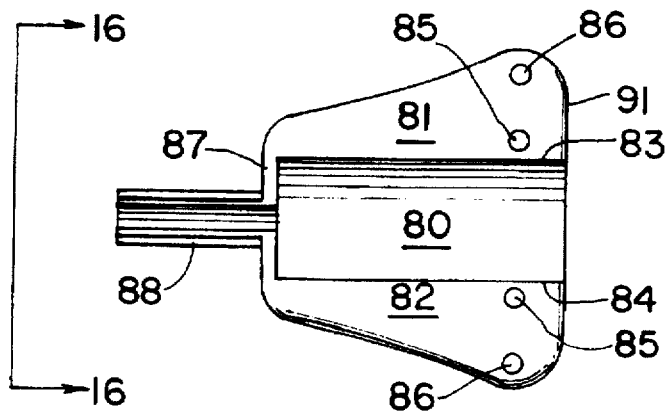
FIG. 13 is a top plan view of a suture template of the present invention.
Figure 14:
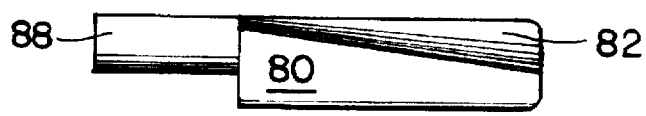
FIG. 14 is a side plan view of the template of FIG. 13.
Figure 15:
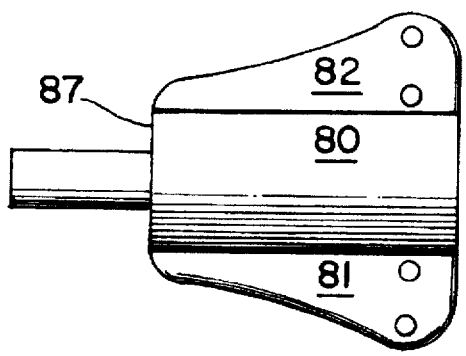
FIG. 15 is a bottom plan view of the template of FIG. 13.
Figure 16:
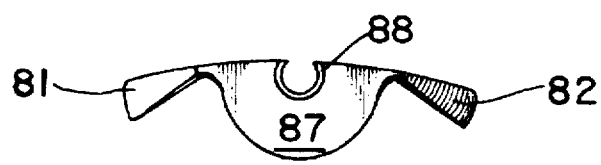
FIG. 16 is an end plan view of the template of FIG. 13, taken along line 16—16 thereof.

It is certainly possible that the template of the present invention may merely be held in place by hand, and in fact the downwardly sloping nature of the underside wing members 81 and 82 are suitable for placement of the surgeon's fingers thereunder. Additional alignment means are preferably provided, however at a minimum, end wall 87 is provided at the end of trough 80 furthest away from the suture guide apertures. Thus, as long as the template is properly sized for the length of the patient's urethra, the surgeon may hold the template in place with end wall 87 abutting the outermost end 89 of urethra 4 in order to ensure proper alignment. For example, if the length of the patient's urethra is determined to be three cm, the distance between end wall 87 and first and second guide apertures 85 and 86 should be between about 2.5 and about 3.2 cm, most preferably about 2.8 cm. The guide apertures should also be between about 0.25 and about 0.5 cm from distal end 91 of the wing members (FIG. 13). As long as the template is positioned with end wall 87 abutting the outermost portion of the urethra, the surgeon will be assured that the sutures will be properly placed without risk of puncturing the bladder, or urethra.

While the surgeon may employ two fingers beneath wing members 81 and 82 to hold the template in the proper position, Applicant has found that the provision of arcuate alignment member 88 secured to end wall 87 may be effectively employed for securing the template in place without the need for the surgeon to hold the template in any manner. Alignment member 88 is preferably positioned parallel to trough 80, with the center line of alignment member 88 aligned with the center line of trough 80. Alignment member 88 may either extend away from trough 80 as shown in FIG. 13, or alternatively may extend away from end wall 87 directly along the interior of trough 80 as shown in FIG. 18.

When the embodiment of FIGS. 13–16 is employed, alignment member 88 is preferably sized so that when the template is manufactured from a resilient material, alignment member 88 may be rigidly snapped about Foley catheter 14 as shown in FIG. 20. Thus, the shaft of Foley catheter will be securely held within alignment member 88, and the surgeon need only pull outwardly on the Foley catheter while sliding the template into the vagina towards the urethra until end wall 87 abuts end 89 of urethra 2. The ball of the Foley catheter will thus be positioned at the UVJ, and the template will likewise be positioned at the appropriate location assuming that a template of the proper size has been selected based upon the length of the urethra.

As an alternative to providing various sizes for the template of the present invention, a single, larger-sized template may be employed provided that alignment member 88 is snapped about the shaft of Foley catheter 14 in the proper location. Thus, instead of abutting end wall 87 against end 89 of urethra 2, end wall 87 is instead aligned with the appropriate graduation along the shaft of Foley catheter 14 based upon the previously-measured length of the urethra. Likewise, end 90 of alignment member 88 could alternatively be aligned with the appropriate graduation along the shaft of Foley catheter 14 in order to provide the proper placement of the template based upon the length of the patient's urethra.

Figure 18:
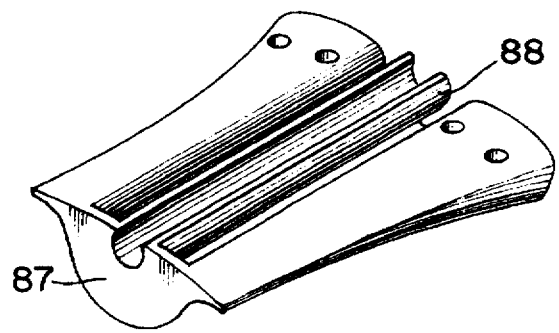
FIG. 18 is a perspective view of an alternative embodiment of the suture template according to the present invention.
Figure 19:
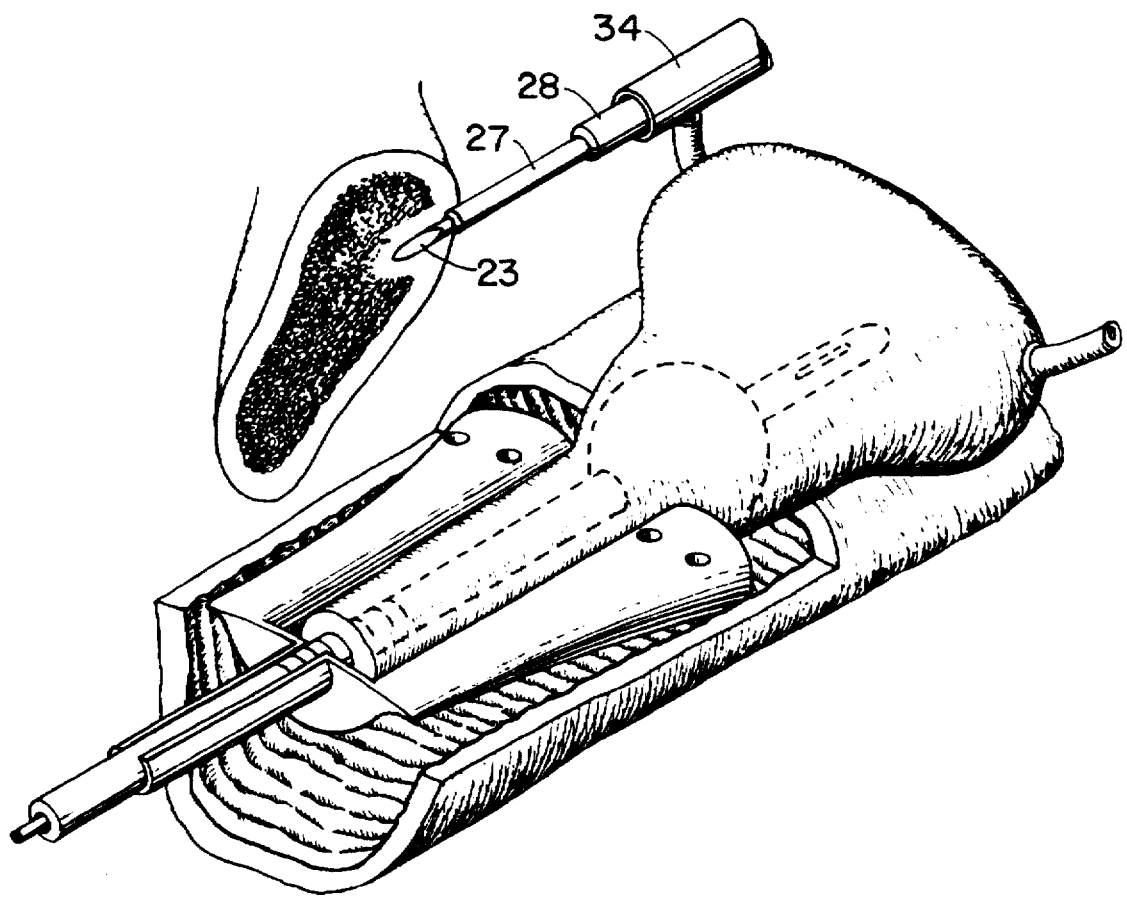
FIG. 19 is a perspective view of the insertion tool of FIG. 8 in use during a surgical procedure with portions of the patient's anatomy cut-away for clarity.

FIG. 18 depicts yet another alternative embodiment for the template of the present invention in which alignment member 88 extends along the interior of trough 80. In employing this embodiment, alignment member 88 is inserted into the urethra along with Foley catheter 13 until end wall 87 of the template abuts end 89 of urethra 2. As will be understood, therefor, an appropriately-sized template will ensure proper placement of the sutures.

Finally, the template of the present invention can be manufactured of any suitable material such as polycarbonate or other FDA-approved plastic. The template may be readily molded using known technology, and is preferably manufactured as a disposable, single-use item. The drill tamper tool and anchor insertion tools, on the other hand, should be made from medical-grade stainless steel. The handles, however, may be polycarbonate or other FDA-approved plastic.

What I claim is:

1. A surgical method for performing laparoscopic urethropexy on a patient, comprising the steps of:
   (a) dissecting at least a portion of the space of Retzius in the patient;
   (b) laparoscopically creating a bore in the pubic bone adjacent the space of Retzius;
   (c) providing at least one anchor, said anchor having at least one suture extending therefrom;
   (d) laparoscopically inserting an anchor in said bore such that said anchor is thereby secured in said bore; and
   (e) securing said suture to the periurethral tissue adjacent to the urethra to thereby elevate the urethra to the desired angle.

2. The surgical method of claim 1, wherein said suture is secured to the periurethral tissue by pulling said suture through the periurethral fascia and vaginal mucosa into the vagina, and tying said suture within the vagina.

3. The surgical method of claim 2, wherein:
   a pair of bores are created in the pubic bone, with one of said bores on either side of the pubic symphysis above the periurethral fascia;
   a pair of anchors are provided, each of said anchors having a suture extending therefrom;
   one of said pair of anchors is inserted into each of said bores; and
   one of said sutures is pulled through the periurethral fascia and vaginal mucosa adjacent either side of the urethra into the vagina; and
   each of said sutures is tied within the vagina, such that one of said sutures will provide an upward force on the periurethral tissue positioned on either side of the urethra, thereby elevating the urethra to the desired angle.

4. The surgical method of claim 1, wherein said bore creation step comprises:
   (a) inserting a laparoscope into the patient to provide access to and vision of the space of Retzius;
   (b) creating a crater in the pubic bone at the desired location for said bore, said crater being sufficiently deep to provide access to the cancellous bone;
   (c) providing a drill tamper tool, said drill tamper tool having a boring tip, said boring tip having a distal end; and
   (d) inserting said boring tip of said drill tamper tool through the laparoscopic channel;
   (e) urging the distal end of said boring tip into said crater to create said bore in the cancellous bone beneath said crater.

5. The surgical method of claim 4, wherein the distal end of said boring tip is sufficiently sharp to enable said tip to create said bore in the cancellous bone by means of hand force, while being insufficiently sharp to inadvertently pierce soft tissue or organs during the bore creation step.

6. The surgical method of claim 4, wherein said drill tamper tool comprises an elongate rigid member having:
   (a) said boring tip;
   (b) a collar having a diameter greater than that of said boring tip;
   (c) a cylindrical guide portion having first and second ends, said guide portion having a diameter greater than said tip and slightly less than the operative channel of said laparoscope; and
   (d) a handle attached to said second end of said guide portion;
   wherein said collar is positioned between said tip and said guide portion such that said first end of said guide portion is nearer said collar than said second end, and wherein said bore is created by inserting said distal end of the boring tip into said crater, and rotatingly urging said boring tip into said crater by means of said handle.

7. The surgical method of claim 6, wherein said collar acts as a stop during said bore creation step such that the length of said bore is approximately equivalent to the length of said boring tip.

8. The surgical method of claim 7, wherein said drill tamper tool further comprises an intermediate portion having a diameter greater than that of said boring tip, said intermediate portion attached to said boring tip at said collar, wherein said collar comprises the end of said intermediate portion positioned adjacent said boring tip.

9. The surgical method of claim 1, wherein said anchor insertion step comprises:
   (a) providing an anchor-insertion tool having said anchor loaded thereon, said anchor-insertion tool comprising an elongate member having:
      an anchor-receiving tip at one end, and
      a handle at the opposite end;
   wherein said anchor is loaded on said tip;
   (b) inserting said anchor into said bore by urging said anchor-receiving tip, with said anchor loaded thereon, toward said bore; and
   (c) pulling said anchor-insertion tool away from said bore, thereby releasing said anchor from said anchor-receiving tip.

10. The surgical method of claim 9, wherein:
    said anchor-insertion tool further comprises an elastic band extending about its circumference;
    said suture is positioned between said elastic band and said anchor-insertion tool so that said suture is securely held against said insertion tool by said elastic band; and
    during said step of pulling said insertion tool away from said bore, said suture is permitted to slide between said elastic band and said insertion tool so that said suture is tensioned between said anchor and said insertion tool.

11. The surgical method of claim 9, wherein:
    after said pulling step said suture extends between said anchor and said insertion tool; and
    said suture securing step comprises:
       (a) providing a suture retriever, said retriever having a tip;
       (b) inserting said tip of said suture retriever into the vagina, through the vaginal mucosa and periurethral fascia adjacent the urethra, towards said suture;
       (c) snaring said tensioned suture with said suture retriever;
       (d) pulling said snared suture into the vagina by means of said suture retriever; and (e) tying said suture within the vagina.

12. The surgical method of claim 9, wherein said at least one suture has first and second tails extending from said anchor, wherein both of said tails extend between said insertion tool and said anchor after said pulling step, and wherein said suture securing step comprises:
   (a) providing a suture retriever, said retriever having a pointed tip;
   (b) inserting said tip of said suture retriever into the vagina, through the vaginal mucosa and periurethral fascia adjacent the urethra, into the space of Retzius;
   (c) snaring said first tail of said at least one suture with said suture retriever;
   (d) pulling said snared first tail into the vagina by means of said suture retriever;
   (e) repeating steps (b)-(d) for the second tail of said at least one suture, wherein said snared second tail is pulled into the vagina a predetermined distance from the first tail; and
   (f) tying said first and second suture tails to each other within the vagina in order to elevate the urethra to the desired angle.

13. The method of claim 12, further comprising the steps of:
   (a) laparoscopically creating a second bore in the pubic bone, such that one of said bores is positioned on either side of the pubic symphysis above the periurethral fascia;
   (b) providing a second anchor having a second suture extending therefrom, said second suture having first and second tails;
   (c) laparoscopically inserting said second anchor in said second bore using said insertion tool such that said second anchor is thereby secured in said second bore;
   (d) inserting said tip of said suture retriever into the vagina, through the vaginal mucosa and periurethral fascia adjacent the urethra, into the space of Retzius;
   (e) snaring said first tail of said second suture with said suture retriever;
   (f) pulling said snared first tail into the vagina by means of said suture retriever;
   (g) repeating steps (d)-(f) for the second tail of said second suture, wherein said snared second tail is pulled into the vagina a predetermined distance from the first tail; and
   (h) tying said first and second tails of said second suture to each other within the vagina in order to elevate the urethra to the desired angle;
wherein said first and second tails of said at least one suture are pulled into the vagina on one side of the urethra, and wherein said first and second tails of said second suture are pulled into the vagina on the opposite side of the urethra, such that after tying one of said sutures will apply an upward force on the periurethral tissue positioned on either side of the urethra, thereby elevating the urethra to the desire angle.

14. The surgical method of claim 10, wherein said anchor-insertion tool further comprises a depression extending about the circumference of said anchor-insertion tool, and wherein said elastic band is positioned within said depression.

15. The surgical method of claim 9, wherein:
   said anchor-insertion tool further comprises a cylindrical intermediate portion having a distal end adjacent said anchor-receiving tip, said intermediate portion having a diameter greater than the diameter of said anchor-receiving tip;

the diameter of said anchor-receiving tip is approximately equivalent to the diameter of said anchor; and
   the combined length of said anchor and said anchor-receiving tip is approximately equivalent to the depth of said bore;
such that during the step of inserting said anchor into said bore, said distal end of said intermediate portion of the anchor-insertion tool acts as a stop, thereby ensuring that the anchor is inserted into said bore to the maximum possible depth.

16. A drill tamper tool for laparoscopically creating a bore in the cancellous portion of the pubic bone of a patient during a urethropexy procedure, said tool comprising an elongate, rigid member having:
   (a) a boring tip, said boring tip having a distal end which is sufficiently sharp to enable said tip to create said bore in cancellous bone by means of hand force;
   (b) a cylindrical guide portion having first and second ends, said guide portion having a diameter greater than said tip, and insertable in the operative channel of a laparoscope;
   (c) a collar having a diameter greater than that of said boring tip, said collar positioned between said tip and said guide portion such that said first end of said guide portion is nearer said collar than said second end, and such that said collar prevents said boring tip from penetrating the pubic bone beyond a predetermined depth; and
   (d) a handle attached to said second end of said guide portion;
wherein the total length of said tool is such that said tool may be readily employed laparoscopically to create a bore in the pubic bone of a patient during a laparoscopic urethropexy procedure by inserting said distal end of the boring tip into a crater previously created in said pubic bone, said crater being sufficiently deep to provide access to the cancellous bone, and rotatingly urging said boring tip into said crater by means of said handle in order to create said bore, said bore having a length corresponding to the length of said boring tip.

17. The drill tamper tool of claim 16, wherein said boring tip has a conical cross section, and flat sides which taper from said distal end of the boring tip to a cylindrical rear portion of the boring tip, wherein the tool may be employed to create a bore having a diameter which corresponds to the diameter of said rear portion.

18. The drill tamper tool of claim 16, wherein said boring tip has a length of between about 1 and about 3 centimeters.

19. The drill tamper tool of claim 18, further comprising an intermediate portion having a diameter greater than that of said boring tip, said intermediate portion positioned between said collar and said guide portion, wherein said intermediate portion has a length of between about 2 and about 6 centimeters.

20. The drill tamper tool of claim 18, wherein said guide portion has a length of at least about 50 centimeters.

21. An anchor-insertion tool for laparoscopically inserting and securing an anchor having a suture extending therefrom within a bore created in the pubic bone of a patient during a urethropexy procedure, said anchor-insertion tool comprising an elongate member having:
   (a) an anchor-receiving tip, said tip capable of holding an anchor thereon;
   (b) a cylindrical guide portion having first and second ends, said guide portion having a diameter greater than said tip and insertable in the operative channel of a laparoscope; and (e) a handle attached to said second end of said guide portion;

wherein said guide portion is positioned between said handle and said tip, and wherein the total length of said anchor-insertion tool is such that said tool may be employed laparoscopically to insert said anchor into a bore in the pubic bone of a patient during a laparoscopic urethropexy procedure.

22. The anchor-insertion tool of claim 21, further comprising at least one depression extending about the circumference of said guide portions, said depression sized so as to accommodate an elastic band for holding said suture between said elastic band and said tool.

23. The anchor-insertion tool of claim 22, further comprising at least one groove extending from said tip and at least partially along the length of said tool.

24. The anchor-insertion tool of claim 22, further comprising a second depression extending about the circumference of said tool, said second depression sized so as to accommodate an elastic band for holding said suture between said elastic band and said tool, wherein both of said depressions extend about said cylindrical guide portion.

25. The anchor insertion tool of claim 22, further comprising an intermediate portion positioned between said tip and said guide portion, wherein said anchor-receiving tip has a pair of guide tabs extending from either side of the end of said tip opposite said intermediate portion, said guide tabs matingly receivable in corresponding grooves on an anchor to thereby hold an anchor on said anchor-receiving tip.

26. The anchor-insertion tool of claim 21, wherein said guide portion has a length of at least about 50 centimeters.

27. A loaded anchor-insertion tool comprising, in combination, an anchor-insertion tool, an anchor having a suture extending therefrom, and at least one elastic band, wherein said anchor-insertion tool comprises an elongate member having:

(a) an anchor-receiving tip;
(b) a handle; and
(c) a cylindrical guide portion positioned between said tip and said handle;

wherein the total length of said anchor-insertion tool is such that said tool may be employed laparoscopically to secure said anchor to the pubic bone of a patient during a laparoscopic urethropexy procedure, wherein said anchor is positioned on said anchor-receiving tip, wherein said elastic band is positioned about said guide portion, and wherein said suture extends along at least a portion of the length of said anchor-insertion tool and is slidably held between said elastic band and said guide portion such that after said anchor has been secured in a patient's body, said anchor-insertion tool may be pulled away from said anchor with said suture sliding between said elastic band and said guide portion.

28. The loaded anchor-insertion tool of claim 27, further comprising:

a depression extending about the circumference of said cylindrical guide portion;

wherein said elastic band is positioned in said depression.

29. The loaded anchor-insertion tool of claim 27, wherein:

(a) said anchor comprises:
  a cylindrical body having a conical end;
  at least two flexible barbs curving outwardly away from said body;
  a cylindrical end portion extending away from said body at an end of said body opposite to said conical end, said end portion having a diameter smaller than said body;
  a pair of grooves extending along a portion of the length of said body from said cylindrical end; and
  an aperture extending through a portion of said cylindrical end and a portion of said body; and (b) said anchor-insertion tool has:
  a pair of guide tabs extending from either side of the end of said tip;
  a cylindrical slot extending through a portion of said tip; and
  a pair of tapered grooves extending along opposite sides of said tip and at least partially along the length of said intermediate portion;

wherein said guide tabs are matingly received in said grooves on said anchor to thereby hold the anchor on said anchor-receiving tip, wherein said suture extends through said aperture on said anchor, and wherein said suture is positioned within said pair of tapered grooves on said anchor-insertion tool.

30. A surgical kit for laparoscopically inserting an anchor into the pubic bone of a patient during an urethropexy procedure, said kit comprising an anchor-insertion tool for inserting an anchor into a bore in the pubic bone of a patient, and a drill tamper tool for creating said bore in the pubic bone for receiving said anchor, said drill tamper tool comprising an elongate, rigid member having:

(a) a boring tip, said boring tip having a distal end which is sufficiently sharp to enable said tip to create said bore in cancellous bone by means of hand force;

(b) a cylindrical guide portion having first and second ends, said guide portion having a diameter greater than said tip, and insertable in the operative channel of a laparoscope;

(c) a collar having a diameter greater than that of said boring tip, said collar positioned between said tip and said guide portion such that said first end of said guide portion is nearer said collar than said second end, and such that said collar prevents said boring tip from penetrating the pubic bone beyond a predetermined depth; and (d) a handle attached to said second end of said guide portion;

wherein the total length of said drill tamper tool is such that said tool may be readily employed laparoscopically in order to create a bore in the pubic bone of a patient during a laparoscopic urethropexy procedure by inserting said distal end of the boring tip into a crater previously created in said pubic bone, said crater being sufficiently deep to provide access to the cancellous bone, and rotatingly urging said boring tip into said crater by means of said handle in order to create said bore, said bore having a length corresponding to the length of said boring tip.

31. A surgical kit for laparoscopically inserting an anchor into the pubic bone of a patient during an urethropexy procedure, said kit comprising a drill tamper tool for creating a bore in the pubic bone, and an anchor-insertion tool for inserting an anchor into said bore, said anchor-insertion tool comprising an elongate member having:

(a) an anchor-receiving tip, said tip capable of holding an anchor thereon;

(b) a cylindrical guide portion having first and second ends, said guide portion having a diameter greater than said tip and insertable in the operative channel of a laparoscope; and (e) a handle attached to said second end of said guide portion;

wherein said guide portion is positioned between said handle and said tip, and wherein the total length of said anchor-insertion tool is such that said tool may be employed laparoscopically in order to insert said anchor into a bore in the pubic bone of a patient during a laparoscopic urethropexy procedure.

32. A surgical method for performing laparoscopic urethropexy on a patient, comprising the steps of:

(a) providing at least one anchor and at least one suture;

(b) laparoscopically securing said anchor to the pubic bone of said patient;

(c) securing said suture between said anchor and the periurethral tissue adjacent the urethra, thereby elevating the urethra to the desired angle.

33. The method of claim 32, further comprising the step of dissecting at least a portion of the space of Retzius prior to the step of securing said anchor, and wherein said anchor is secured to the pubic bone adjacent the space of Retzius.

34. The method of claim 32, further comprising the step of laparoscopically creating a bore in the pubic bone, and said step of securing said anchor to the pubic bone comprises laparoscopically inserting said anchor into said bore such that the anchor is secured within the bore.

35. The method of claim 32, wherein said anchor is provided with said suture extending therefrom, and said step of securing said suture between said anchor and the periurethral tissue comprises the steps of pulling said suture through the periurethral fascia and vaginal mucosa into the vagina, and tying said suture within the vagina.

36. The method of claim 33, wherein:

a pair of anchors are provided, each of said anchors having a suture extending therefrom;

each anchor is secured to the pubic bone adjacent the space of Retzius; and each of said sutures is secured to the periurethral tissue adjacent to the urethra by pulling said suture through the periurethral fascia and vaginal mucosa into the vagina, and tying said suture within the vagina.

37. The method of claim 35, wherein said step of pulling said suture through the periurethral fascia and vaginal mucosa into the vagina comprises the steps of:

(a) providing a suture retriever, said retriever having a tip;

(b) inserting said tip of said suture retriever into the vagina, through the vaginal mucosa and periurethral fascia adjacent the urethra into the patient;

(c) grasping said suture with said retriever;

(d) pulling said tip of said retriever back into the vagina, thereby pulling said suture into the vagina.

38. The method of claim 35, further comprising the steps of:

(a) providing a suture template, said template having at least one guide aperture; and (b) positioning said template within the vagina of the patient, such that said aperture is alignably positioned against the vaginal mucosa adjacent the urethra;

and wherein said suture is pulled through said guide aperture of said template.

39. The method of claim 35, wherein said suture has first and second tails, each tail is pulled through the periurethral fascia and vaginal mucosa into the vagina such that said first tail is located a predetermined distance from said second tail, and wherein said tying step comprises tying said first tail to said second tail.

40. The surgical method of claim 1, wherein said bore creation step comprises:

(a) creating a crater in the pubic bone at the desired location for said bore;

(b) providing a drill tamper tool, said drill tamper tool having a boring tip, said boring tip having a distal end; and (c) urging the distal end of said boring tip into said crater to create said bore in the cancellous bone beneath said crater.

41. The method of claim 40, wherein said crater is created by means of a laser.

42. The method of claim 7, wherein said collar is tapered.

43. The loaded anchor-insertion tool of claim 28, further comprising a second elastic band and a second depression extending about said guide portion, wherein said second elastic band is positioned in said second depression and said suture is slidably held between said second elastic band and said guide portion.

44. The surgical kit of claim 30, further comprising a surgical template positionable within the vagina of a patient for guiding a portion of a suture extending from an anchor secured to the pubic bone of a patient into the patient's vagina.

45. The surgical kit of claim 31, further comprising a surgical template positionable within the vagina of a patient for guiding a portion of a suture extending from an anchor secured to the pubic bone of a patient into the patient's vagina.

46. The surgical kit of claim 30, further comprising a suture retrieval tool for vaginally retrieving a portion of a suture extending from an anchor secured to the pubic bone of a patient, said retrieval tool having a retrieving end and a handle.

47. The surgical kit of claim 31, further comprising a suture retrieval tool for vaginally retrieving a portion of a suture extending from an anchor secured to the pubic bone of a patient, said retrieval tool having a retrieving end and a handle.

48. The surgical method of claim 32, wherein said step of securing said anchor to the pubic bone comprises:

(a) providing an anchor-insertion tool comprising an elongate member having an anchor-receiving tip at one end and a handle at the opposite end wherein said anchor is positioned on said tip with said suture extending from said anchor;

(b) inserting a laparoscope into the patient to provide access to said pubic bone;

(c) inserting the tip of said insertion tool into the operative channel of said laparoscope;

(d) inserting said anchor into a bore in said pubic bone by urging said tip of the insertion tool towards said bore, thereby securing said anchor within said pubic bone; and (e) pulling said insertion tool away from said bore and said anchor by means of said handle.

49. The surgical method of claim 48, wherein after said step of pulling said insertion tool away from said bore and said anchor, said suture extends between said anchor and said insertion tool.

50. The surgical method of claim 49, wherein said suture is slidably secured to said insertion tool.

51. The surgical method of claim 50, wherein at least one elastic band extends around said insertion tool, and wherein said suture is slidably secured to said insertion tool by positioning said suture between said elastic band and said insertion tool.

52. The surgical method of claim 51, wherein said anchor-insertion tool further comprises a cylindrical guide portion positioned between said tip and said handle, said guide portion having at least one depression extending about its circumference, and wherein said elastic band is positioned within said depression.

53. The surgical method of claim 52, wherein said anchor-insertion tool further comprises a second depression extending about the circumference of said guide portion, wherein a second elastic band is positioned within said second depression, and said suture if further slidably secured between said second elastic band and said insertion tool.

54. The surgical method of claim 51, wherein said elastic band provides tension in said suture during said step of pulling said insertion tool away from said bore, such that said tension pulls outwardly on said anchor thereby further securing said anchor within said bore.

55. The method of claim 34, wherein said step of creating a bore in the pubic bone comprises:

(a) providing a drill tamper tool comprising a rigid, elongate member having a boring tip at one end and a handle at the opposite end, said boring tip having a distal end;

(b) inserting a laparoscope into the patient to provide access to said pubic bone;

(c) creating a crater in the pubic bone at the desired location for said bore; (d) inserting the boring tip of said drill tamper tool into the operative channel of said laparoscope;

(e) urging said boring tip into said crater to create said bore in the cancellous bone beneath said crater.

56. The surgical method of claim 55, wherein said drill tamper tool has a tapered collar adjacent said boring tip, wherein said collar acts as a stop during said step of urging said boring tip into said crater, thereby ensuring that the length of said bore corresponds approximately to the length of said boring tip.

57. A surgical method for laparoscopically creating a bore in the pubic bone of a patient, comprising the steps of:

(a) inserting a laparoscope into the patient to provide access to and vision of the space of Retzius;

(b) creating a crater in the pubic bone at the desired location for said bore;

(c) providing a drill tamper tool, said tool having a boring tip, said boring tip having a distal end;

(d) inserting said boring tip through the operative channel of the laparoscope; and (e) urging the distal end of said boring tip into the crater to create said bore.

58. The method of claim 57, wherein said crater is created with a laser.

59. The method of claim 57, wherein said drill tamper tool comprises an elongate rigid member having:

(a) said boring tip;

(b) a collar having a diameter greater than that of said boring tip;

(c) a cylindrical guide portion having first and second ends, said guide portion having a diameter greater than said tip and slightly less than the operative channel of said laparoscope; and (d) a handle attached to said second end of said guide portion;

wherein said collar is positioned between said tip and said guide portion such that said first end of said guide portion is nearer said collar than said second end, and wherein said boring tip is rotatingly urged into said crater by means of said handle in order to create said bore.

60. The method of claim 59, wherein said collar acts as a stop such that the length of said bore is approximately equivalent to the length of said boring tip.

* * * * *